(12) United States Patent
Naito et al.

(10) Patent No.: US 12,318,495 B2
(45) Date of Patent: *Jun. 3, 2025

(54) ULTRAVIOLET LIGHT IRRADIATION DEVICE, METHOD OF USING ULTRAVIOLET LIGHT IRRADIATION DEVICE, AND ULTRAVIOLET LIGHT IRRADIATION METHOD

(71) Applicant: Ushio Denki Kabushiki Kaisha, Tokyo (JP)

(72) Inventors: Keisuke Naito, Tokyo (JP); Hideaki Yagyu, Tokyo (JP); Akihiro Kuno, Tokyo (JP); Shigeki Fujisawa, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 827 days.

This patent is subject to a terminal disclaimer.

(21) Appl. No.: 17/610,424

(22) PCT Filed: Aug. 20, 2021

(86) PCT No.: PCT/JP2021/030572
§ 371 (c)(1),
(2) Date: Nov. 10, 2021

(87) PCT Pub. No.: WO2022/074944
PCT Pub. Date: Apr. 14, 2022

(65) Prior Publication Data
US 2023/0248857 A1    Aug. 10, 2023

(30) Foreign Application Priority Data

Oct. 8, 2020 (JP) .................................. 2020-170693
Apr. 14, 2021 (JP) .................................. 2021-068405

(51) Int. Cl.
*A61L 2/10* (2006.01)
*A61L 2/26* (2006.01)
(Continued)

(52) U.S. Cl.
CPC .................. *A61L 2/10* (2013.01); *A61L 2/26* (2013.01); *H01J 61/025* (2013.01); *H01J 61/40* (2013.01); *A61L 2202/11* (2013.01)

(58) Field of Classification Search
CPC ........................................................ A61L 2/10
See application file for complete search history.

(56) References Cited

U.S. PATENT DOCUMENTS

2018/0236113 A1* 8/2018 Gross .................... G02B 5/008
2019/0099613 A1* 4/2019 Estes .................... A61N 5/0616
(Continued)

FOREIGN PATENT DOCUMENTS

CN  109966652 A   7/2019
JP  S63-187221 U  11/1988
(Continued)

OTHER PUBLICATIONS

Reconsideration Report by Examiner before Appeal issued by the Japanese Patent Office, dated Jun. 7, 2022, which corresponds to Japanese Patent Application No. 2020-170693 and is related to U.S. Appl. No. 17/610,424; with English language translation.
(Continued)

*Primary Examiner* — Kevin Joyner
(74) *Attorney, Agent, or Firm* — Studebaker Brackett PLLC

(57) ABSTRACT

Provided is an ultraviolet light irradiation device that is capable of causing effective inactivation of microorganisms as well as a method of using the ultraviolet light irradiation device.
An ultraviolet light irradiation device includes a light source that radiates ultraviolet light with a wavelength in a range of
(Continued)

190 nm to 235 nm; a housing that houses the light source; an extracting portion that extracts the ultraviolet light that is radiated from the light source and causes it to be directed toward an exterior of the housing; and a diffusing member that diffuses the ultraviolet light.

17 Claims, 11 Drawing Sheets

(51) Int. Cl.
    *H01J 61/02*     (2006.01)
    *H01J 61/40*     (2006.01)

(56) References Cited

U.S. PATENT DOCUMENTS

| | | |
|---|---|---|
| 2019/0192708 A1 | 6/2019 | Igarashi |
| 2019/0192709 A1 | 6/2019 | Igarashi |
| 2020/0215214 A1 | 7/2020 | Rosen et al. |
| 2021/0379215 A1* | 12/2021 | Kelleher .................. A61L 2/10 |
| 2022/0042910 A1* | 2/2022 | Qi ...................... G01N 21/6458 |
| 2023/0248857 A1 | 8/2023 | Naito et al. |

FOREIGN PATENT DOCUMENTS

| | | |
|---|---|---|
| JP | H06-073296 A | 3/1994 |
| JP | H11-000386 A | 1/1999 |
| JP | 2002-042519 A | 2/2002 |
| JP | 2009-050584 A | 3/2009 |
| JP | 2014-508612 A | 4/2014 |
| JP | 2017-018442 A | 1/2017 |
| JP | 2018-191840 A | 12/2018 |
| JP | 2019-115525 A | 7/2019 |
| JP | 2022-062580 A | 4/2022 |
| KR | 10-0998473 B1 | 12/2010 |
| WO | 2012/122210 A1 | 9/2012 |
| WO | 2021/117276 A1 | 6/2021 |

OTHER PUBLICATIONS

The extended European search report issued by the European Patent Office on Jun. 17, 2022, which corresponds to European Patent Application No. 21794298.6-1012 and is related to U.S. Appl. No. 17/610,424.
Communication pursuant to Article 94(3) EPC issued by the European Patent Office on Sep. 2, 2024, which corresponds to European Patent Application No. 21794298.6-1009.
The extended European search report issued by the European Patent Office on Sep. 12, 2024, which corresponds to European Patent Application No. 22788082.0-1009.
International Search Report issued in PCT/JP2021/030572; mailed Sep. 21, 2021.
Office Action issued in JP 2020-170693; mailed by the Japanese Patent Office on Aug. 19, 2021.
An Office Action mailed by China National Intellectual Property Administration on Sep. 13, 2023, which corresponds to Chinese Patent Application No. 202180002568.5; with English language translation.
An Office Action mailed by China National Intellectual Property Administration on Mar. 6, 2024, which corresponds to Chinese Patent Application No. 202180002568.5; with English language translation.
Decision of Refusal mailed by China National Intellectual Property Administration on Jul. 18, 2024, which corresponds to Chinese Patent Application No. 202180002568.5; with English language translation.
Notification of Transmittal of Copies of Translation of the International Preliminary Report on Patentability and Translation of Written Opinion of the International Searching Authority; PCT/JP2022/016712; mailed on Oct. 26, 2023.
International Search Report issued in PCT/JP2022/016712; mailed Jun. 14, 2022.
An Office Action; "Notification of Reasons for Refusal", mailed by the Japanese Patent Office on Dec. 24, 2021, which corresponds to Japanese Patent Application No. 2020-170693 and is related to U.S. Appl. No. 17/610,424; with English language translation.
English Translation of Written Opinion of the International Searching Authority; PCT/JP2021/030572; mailed on Jan. 7, 2022.
"Trial and Appeal Decision" mailed by the Japanese Patent Office on Mar. 8, 2024, which corresponds to Japanese Patent Application No. 2020-170693; with English language translation.
An Office Action; "Notice of Reasons for Refusal," mailed by the Japanese Patent Office on Jul. 3, 2024, which corresponds to Japanese Patent Application No. 2022-046393; with English language translation.

\* cited by examiner

ULTRAVIOLET LIGHT IRRADIATION DEVICE, METHOD OF USING ULTRAVIOLET LIGHT IRRADIATION DEVICE, AND ULTRAVIOLET LIGHT IRRADIATION METHOD

TECHNICAL FIELD

This invention relates to an ultraviolet light irradiation device, a method of using an ultraviolet light irradiation device, and an ultraviolet light irradiation method.

BACKGROUND ART

It is known that bacteria, fungi, viruses, and other such microorganisms exhibit characteristics such that absorption is highest in the vicinity of a wavelength of 260 nm. For this reason, a technique has conventionally been known in which ultraviolet light exhibiting a spectrum in which emission is high in the vicinity of a wavelength of 254 nm is irradiated so as to be directed toward a space or surface of an object at which microorganisms are present to cause inactivation of microorganisms.

Patent Reference No. 1 for example describes installing a germicidal lamp that emits ultraviolet light at a kitchen or the like to kill microorganisms at a kitchen. Furthermore, Patent Reference No. 2 describes killing microorganisms by causing viruses and bacteria which float about indoors to be irradiated with ultraviolet light.

In addition, the ultraviolet light irradiation devices described at Patent Reference No. 1 and Patent Reference No. 2 employ ultraviolet light which is harmful to humans. For this reason, measures are adopted such as imparting directionality to the ultraviolet light emitted therefrom so that ultraviolet light is not directed at humans.

PRIOR ART REFERENCES

Patent References

Patent Reference No. 1: Japanese Publication of unexamined utility model application No. S63[1988]-187221
Patent Reference No. 2: Japanese Publication of unexamined patent application No. 2017-018442

SUMMARY OF INVENTION

Problem to be Solved by Invention

However, bacteria, fungi, viruses, and other such microorganisms are especially abundant on surfaces of humans (e.g., hair of the head and skin), on surfaces of objects with which people frequently come in contact (e.g., furniture and office equipment), and in spaces around humans.

Due to the danger of irradiating humans with harmful ultraviolet light, it has not been possible with conventional ultraviolet light irradiation devices to cause ultraviolet light to be irradiated so as to be directed toward surfaces of humans, surfaces of objects with which people frequently come in contact, spaces around humans, and other such vital places at which inactivation of microorganisms would be most in need of being carried out. There has therefore been a limit to the inactivation of microorganisms that has been achievable with conventional ultraviolet light irradiation devices.

The present invention provides an ultraviolet light irradiation device that is capable of causing effective inactivation of microorganisms while ensuring the safety of humans, as well as a method of using the ultraviolet light irradiation device.

Means for Solving Problem

Not all wavelength bands of ultraviolet light present a hazard to humans. While UVC waves of 240 nm and higher have been reported to be hazardous to human cells, because ultraviolet light of shorter wavelength bands than this has little ability to penetrate human cells, the hazard to humans therefrom is extremely low. To cause inactivation of microorganisms while suppressing the hazard to humans, the present inventor(s) therefore focused their attention on use of ultraviolet light for which the primary emission wavelength is 190 nm to 235 nm.

An ultraviolet light irradiation device for causing inactivation of microorganisms in accordance with the present invention includes
  a light source that radiates ultraviolet light with a wavelength in a range of 190 nm to 235 nm;
  a housing that houses the light source;
  an extracting portion that extracts the ultraviolet light that is radiated from the light source and causes it to be directed toward an exterior of the housing; and
  a diffusing member that diffuses the ultraviolet light.

This ultraviolet light irradiation device is such that because ultraviolet light within a wavelength band of 240 nm and higher which is thought to be harmful to humans is suppressed, it is possible to employ a diffusing member and increase the angular divergence of the ultraviolet light. As a result, it is possible to cause places (including surfaces of humans, surfaces of objects with which people frequently come in contact, spaces around humans, and spaces in which people are not present) within which microorganisms are to be inactivated to be irradiated with ultraviolet light over a wide area and without nonuniformity (with little nonuniformity). It will therefore be possible to cause effective inactivation of microorganisms while ensuring the safety of humans.

Throughout the present specification, what is referred to as microorganisms includes protists in general which have cell structures and viruses which do not have cell structures, the protists in general include bacteria which is in prokaryotes and fungi which is eukaryotes such as mold, and the viruses have nucleic acid of DNA/RNA as genome.

Throughout the present specification, what is referred to as inactivation in the case of protists indicates killing as a result of destruction of intracellular DNA, enzyme (protein), and/or the cell membrane or the like, or elimination of ability of cells to reproduce. What is referred to as inactivation in the case of viruses indicates loss of ability to infect cells as a result of destruction of DNA and/or RNA. Viruses, which are contained in aerosols and droplets scattered in the form of sneezes, coughs, spit, and exhaled air from the noses and mouths of people and animals, float across spaces and adhere to surfaces of humans as well as of furniture, floors, walls, and other such objects.

The primary emission wavelength of the ultraviolet light radiated by the light source may be 190 nm to 235 nm. Throughout the present specification, what is referred to as the "primary emission wavelength" indicates, where wavelength bands $Z(\lambda)$ that are ±10 nm with respect to a given wavelength $\lambda$ are defined throughout an emission spectrum, the wavelength $\lambda i$ of the wavelength band $Z(\lambda i)$ for which the integrated intensity is not less than 40% of the total integrated intensity within the emission spectrum. For example, where, as might be the case with an excimer lamp or the like that is filled with a light-emitting gas which contains KrCl, KrBr, or ArF, a light source is such that the full width at half maximum is extremely narrow and luminous intensity is exhibited at only a particular wavelength, the wavelength at which relative irradiance is highest (the primary peak wavelength) may ordinarily be taken to be the primary emission wavelength.

The ultraviolet light irradiation device may further include an optical filter that transmits ultraviolet light within a wavelength band that is not less than 190 nm and not greater than 235 nm but substantially does not transmit ultraviolet light within a wavelength band of 240 nm to 300 nm. By not transmitting ultraviolet light within a wavelength band of 240 nm to 300 nm, for which there is a possibility that there could be an effect on humans, safety for humans is improved. Moreover, to further increase safety for humans, the optical filter may be made to transmit ultraviolet light of wavelength not less than 200 nm and not greater than 230 nm but to substantially not transmit ultraviolet light of 230 nm to 280 nm.

The optical filter and the diffusing member may be arranged at the extracting portion; and the optical filter may be disposed between the light source and the diffusing member.

The ultraviolet light irradiation device may be such that it further includes a reflecting member that is within the housing and that reflects light radiated by the light source. This will increase the irradiance of the light that exits the ultraviolet light irradiation device.

A primary material from which the diffusing member is constituted may be quartz glass, fluororesin, polyethylene, or PET.

Furthermore, the ultraviolet light irradiation device may be made to further include an optical filter that transmits ultraviolet light within a wavelength band that is not less than 190 nm and not greater than 235 nm but substantially does not transmit ultraviolet light within a wavelength band of 240 nm to 280 nm, as a result of which ultraviolet light within a wavelength band of 240 nm to 280 nm, for which there is a possibility that there could be an effect on humans, will not be transmitted therethrough and safety for humans will be improved.

Moreover, to further increase safety for humans, the optical filter may be made to transmit ultraviolet light of wavelength not less than 200 nm and not greater than 230 nm but to substantially not transmit ultraviolet light of 230 nm to 280 nm.

The diffusing member may be arranged so as to come in contact with the optical filter. While described in further detail below, this will make it possible to suppress the backwardly reflected light that is made to return from the diffusing member to as far as the interior of the housing, and will make it possible to improve optical irradiation efficiency. It will moreover facilitate support of thin diffusing members.

The diffusing member may be a diffusing sheet.

A primary constituent of the diffusing sheet may be PTFE.

It may include a securing portion that secures the diffusing sheet at a periphery of the extracting portion. It may include a securing portion that clamps the outside circumference of the diffusing sheet and secures it in place.

The diffusing member may be a diffusing film which is formed on the optical filter.

A primary constituent of the diffusing film may be silica or alumina.

The diffusing member may be arranged so as to be interposed between the optical filter and a transmissive plate that transmits the ultraviolet light.

The diffusing member may be less than 1 mm in thickness.

The diffusing member may be less than 0.5 mm in thickness.

The light source may be an excimer lamp.

A method of using an ultraviolet light irradiation device in accordance with the present invention includes arranging the ultraviolet light irradiation device such that irradiation by at least a portion of ultraviolet light that exits therefrom is directed toward a space used by humans, causing the ultraviolet irradiation device to radiate the ultraviolet light.

An ultraviolet light irradiation device in accordance with the present invention includes a light source that radiates ultraviolet light with a wavelength in a range of 190 nm to 235 nm; a housing that houses the light source; an extracting portion that extracts the ultraviolet light that is radiated from the light source and causes it to be directed toward an exterior of the housing; and an optical filter that is disposed at the extracting portion and that transmits ultraviolet light within a wavelength band of 190 nm to 235 nm but substantially does not transmit ultraviolet light within a wavelength band of 240 nm to 280 nm; wherein the housing has an attachment portion that is disposed at the extracting portion and that is for attachment, at a location toward where the ultraviolet light exits the optical filter, of a diffusing member that diffuses the ultraviolet light.

An ultraviolet light irradiation method in accordance with the present invention includes causing ultraviolet light to be radiated from a light source that radiates ultraviolet light with a wavelength in a range of 190 nm to 235 nm; causing the ultraviolet light radiated from the light source to be selectively transmitted by an optical filter that transmits ultraviolet light within a wavelength band of 190 nm to 235 nm but substantially does not transmit ultraviolet light within a wavelength band of 240 nm to 280 nm; and causing light that exits the optical filter to be diffused by a diffusing member that is arranged toward an exit side of the optical filter.

Effects of Invention

This will make it possible to provide an ultraviolet light irradiation device that is capable of causing effective inactivation of microorganisms as well as a method of using the ultraviolet light irradiation device.

EMBODIMENTS FOR CARRYING OUT INVENTION

Figure 1:
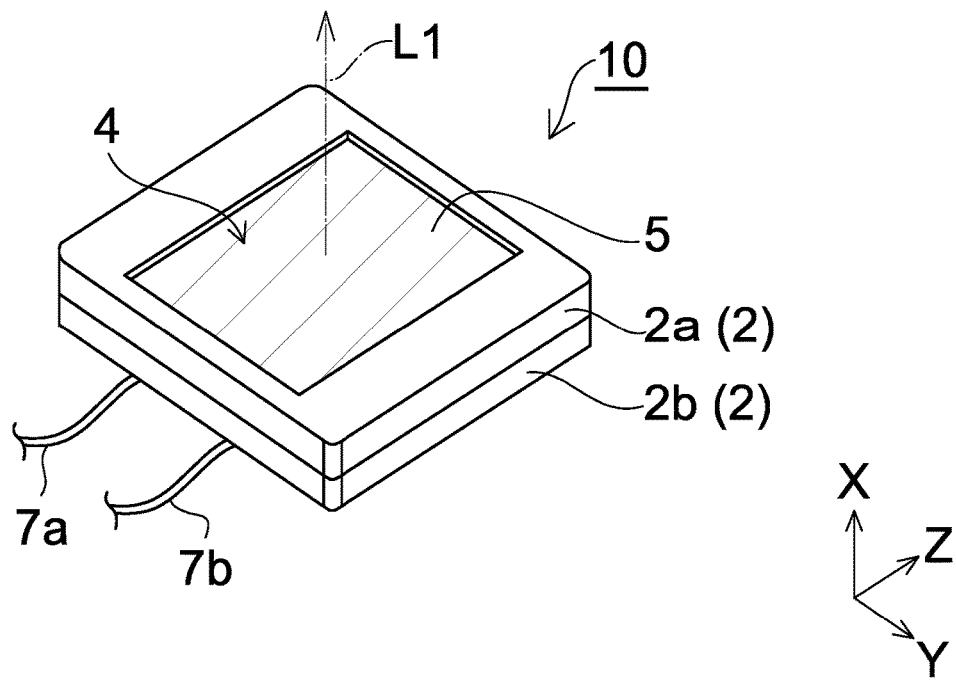
FIG. 1 Perspective view showing in schematic fashion the external appearance of an ultraviolet light irradiation device.

Respective embodiments of ultraviolet light irradiation devices will be described with reference to the drawings. As the following respective drawings are schematic representations, note that the dimensional ratios shown in the drawings are not necessarily consistent with actual dimensional ratios, nor are the dimensional ratios shown necessarily consistent between respective drawings.

Below, description of the respective drawings may be carried out with reference to an XYZ coordinate system as appropriate. At the XYZ coordinate system, the +X direction is taken to be the direction in which a ray of radiated ultraviolet light would proceed along the optical axis, and the YZ plane is taken to be a plane perpendicular to the X direction. Throughout the present specification, in referring to directions, where a distinction is to be made between positive and negative senses of a direction, note that this will be indicated by appending a plus or minus sign thereto as in the "+X direction" and the "-X direction". Where no distinction is to be made between positive and negative senses of a direction, reference will be made to simply the "X direction". That is, throughout the present specification, when reference is made to simply the "X direction", this should be understood to include both the "+X direction" and the "-X direction". The same thing is likewise true with respect to the Y direction and the Z direction.

First Embodiment

Overview of Ultraviolet Light Irradiation Device

Figure 2:
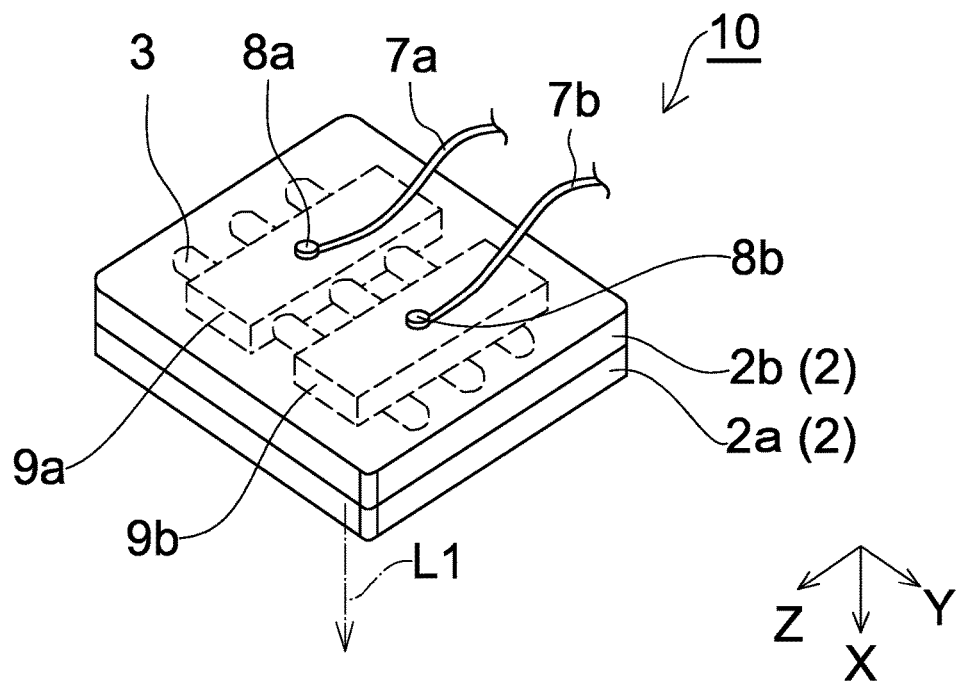
FIG. 2 Perspective view showing in schematic fashion the external appearance of an ultraviolet light irradiation device.
Figure 3:
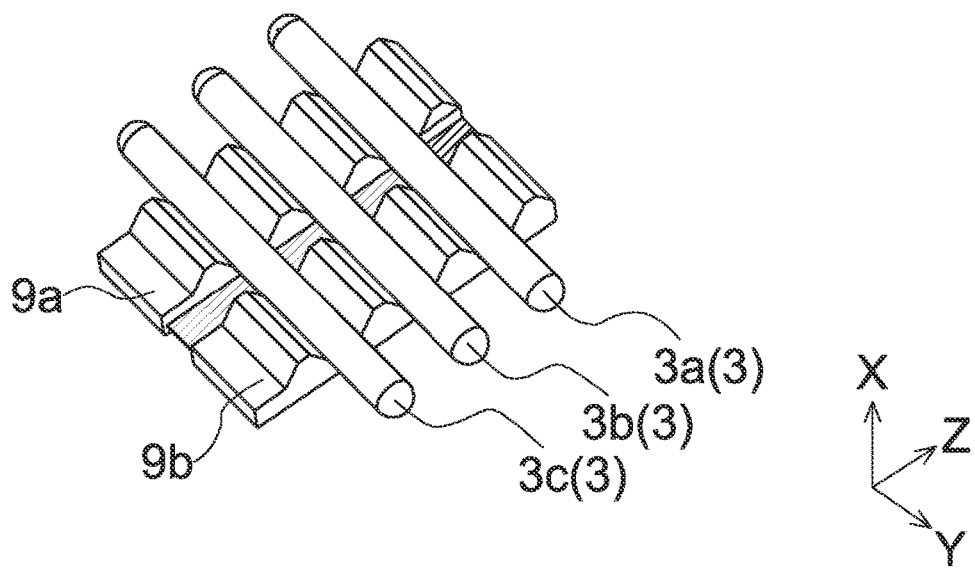
FIG. 3 Perspective view showing only the light sources and electrode blocks which have been removed from an ultraviolet light irradiation device.

A first embodiment of an ultraviolet light irradiation device in accordance with the present invention will be described with reference to FIG. 1, FIG. 2, and FIG. 3. FIG. 1 and FIG. 2 are perspective views showing in schematic fashion the external appearance of an ultraviolet light irradiation device. FIG. 3 is a drawing showing only the light sources and electrode blocks which have been removed from the ultraviolet light irradiation device.

An ultraviolet light irradiation device 10 in accordance with the present embodiment has an excimer lamp 3 (see FIG. 2 and FIG. 3) that radiates ultraviolet light, a housing 2 that houses the excimer lamp 3, an extracting portion 4 that extracts the ultraviolet light which is radiated from the excimer lamp 3 and causes it to be directed in the +X direction toward the exterior of the housing 2, a diffusing member 5 that diffuses the ultraviolet light, and an optical filter 6 which is described below. At FIG. 1 and FIG. 2, arrow L1 indicates the optical axis of the ultraviolet light that is emitted from the excimer lamp 3, and the direction in which a light ray would proceed along the optical axis.

In accordance with the present embodiment, the housing 2 is composed of a first frame 2a which has an opening constituting the extracting portion 4 at the center thereof, and a second frame 2b which does not have an opening, the second frame 2b and the first frame 2a being mated with each other to form an internal space that is bounded by the housing 2. The excimer lamp 3, and two electrode blocks (9a, 9b) which supply electric power to the excimer lamp 3, are arranged within this internal space.

The two electrode blocks (9a, 9b) are secured to a surface that is in contact with the internal space of the second frame 2b (see FIG. 2 and FIG. 3). Provided at a surface that is in contact with the exterior of the second frame 2b are two connection terminals (8a, 8b). The two connection terminals (8a, 8b) respectively make electrical contact with the electrode blocks (9a, 9b) such that the second frame 2b is interposed therebetween. Respectively connected to the two connection terminals (8a, 8b) are electricity supply cables (7a, 7b) to which electric power is supplied from an external power supply (not shown). Note that the two electrode blocks (9a, 9b) are composed of an electrically conductive material (e.g., Al, Al alloy, stainless steel, or the like).

Light Source

An embodiment of an excimer lamp 3 will be described with reference to FIG. 3. In accordance with the present embodiment, excimer lamps 3 are provided in the form of three excimer lamps 3 (3a, 3b, 3c) which are arranged so as to be separated in the Z direction. The two electrode blocks (9a, 9b) make contact with the outer surfaces of the light-emitting tubes of the respective excimer lamps 3 (3a, 3b, 3c). This makes it possible for electricity to be supplied to the excimer lamps 3 so that they may be lit.

In accordance with the present embodiment, the excimer lamps 3 employ KrCl excimer lamps at which a light-emitting gas that contains KrCl is present within the interiors of the light-emitting tubes. For this reason, the excimer lamps 3 radiate ultraviolet light having a primary peak wavelength of 190 nm to 235 nm. In particular, the KrCl excimer lamps emit ultraviolet light having a primary peak wavelength in the vicinity of 222 nm.

The excimer lamps 3 are not limited to KrCl excimer lamps. For example, KrBr excimer lamps at which a light-emitting gas that contains KrBr is present within the interiors of the light-emitting tubes may be employed. KrBr excimer lamps emit ultraviolet light having a primary peak wavelength in the vicinity of 207 nm.

The sizes of the light-emitting tubes of the excimer lamps 3 (3a, 3b, 3c) might be such that the lengths thereof in the tube axis direction (Y direction) are not less than 15 mm and not greater than 200 mm, and such that the outside diameters thereof are not less than 2 mm and not greater than 16 mm.

Overview of Diffusing Member

Figure 4:
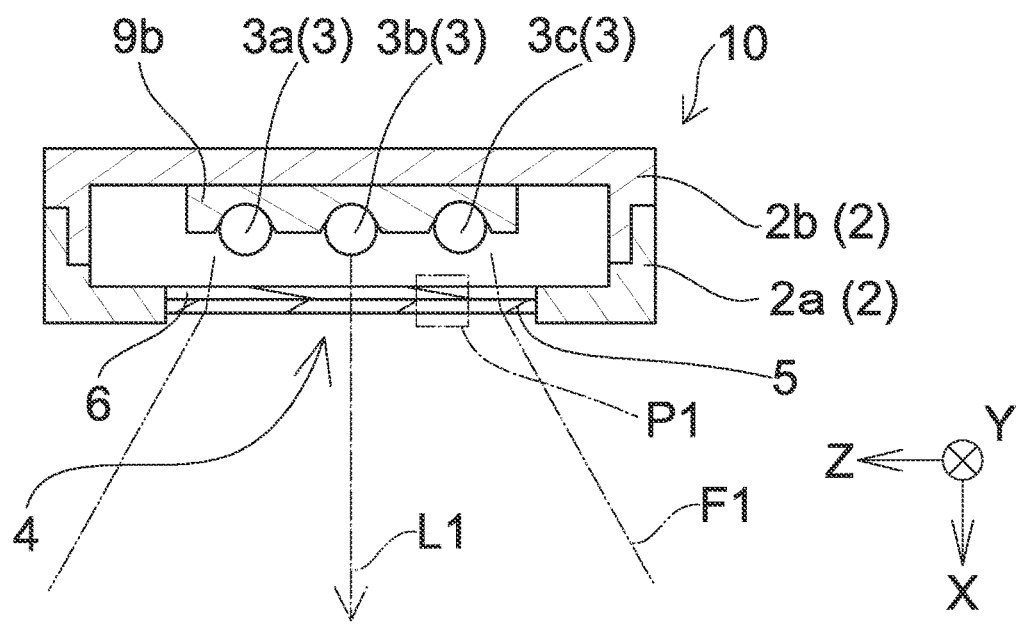
FIG. 4 Sectional schematic view of the XZ plane at an ultraviolet light irradiation device.

FIG. 4 is a sectional schematic view of the XZ plane at an ultraviolet light irradiation device 10. At an ultraviolet light irradiation device 10 in accordance with the present embodiment, an optical filter 6 and a diffusing member 5 which diffuses ultraviolet light are arranged at an opening constituting an extracting portion 4. Note that the expression "arranged at extracting portion" includes not only situations in which the diffusing member 5 and/or the optical filter 6 is/are arranged so as to be completely integral with the light-extracting surface but also situations in which the diffusing member 5 and/or the optical filter 6 is/are arranged at location(s) separated by small distance(s) (e.g., several mm to a dozen or so mm) in the X direction from the light-extracting surface.

Specific wavelength band(s) of the light radiated from the excimer lamps 3 (3a, 3b, 3c) is/are blocked by the optical filter 6. Detailed description of the optical filter 6 will be given below. A bundle of rays F1 emitted from the optical filter 6 is diffused by the diffusing member 5, causing the angle by which the light spreads, i.e., the angular divergence thereof, to increase in magnitude.

Figure 5:
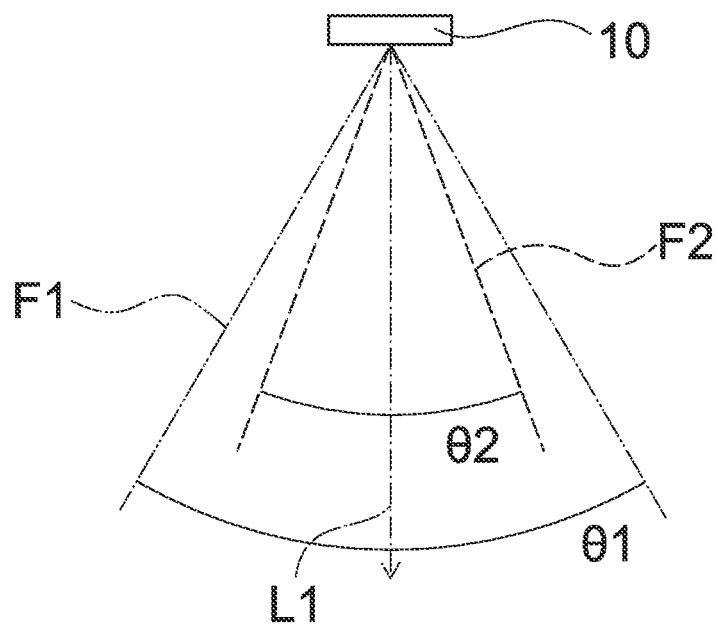
FIG. 5 Drawing for explaining an effect by which the angular divergence of emitted light is increased by a diffusing member.

Description of the increase in magnitude of the angular divergence of the emitted light, this being an effect of the diffusing member 5, will be given with reference to FIG. 5. At FIG. 5, in a hypothetical situation in which a diffusing member is not present, a bundle of rays F2 of ultraviolet light from an ultraviolet light irradiation device 10 might be emitted with an angular divergence $\theta 2$ centered on the optical axis (arrow L1). Where a diffusing member 5 is present, a bundle of rays F1 of ultraviolet light might be emitted with an angular divergence $\theta 1$. The angular divergence $\theta 1$ when a diffusing member 5 is present is greater than the angular divergence $\theta 2$ when a diffusing member is not present. The angular divergence ($\theta 1$, $\theta 2$) is defined as the angle mutually formed by those rays of light within the expanding bundle of rays (F1, F2) of light centered on the optical axis that are at opposite outermost locations most distant from the optical axis. Note that the bundle of rays (F1, F2) of light expands about the optical axis on which it is centered, and is defined as the bundle of rays of light that have luminances not less than ½ of the luminance of a ray of light at the optical axis L1.

Because the diffusing member 5 increases the angular divergence of the emitted light, the ultraviolet light irradiation device 10 is able to cause ultraviolet light to be irradiated over a broad locus. This makes for superior cost-performance, in that it will be possible using a small number of ultraviolet light irradiation devices to provide coverage across a region within which microorganisms are to be inactivated.

Description will next be given with respect to suppression of nonuniformity in the emitted light, which is another effect of the diffusing member 5. Absence of (or presence of little) nonuniformity, because it reduces those regions in which the intensity of the light that locally impinges thereon is weak, reduces those regions in which the inactivation effect is small. Moreover, because it reduces those regions in which the intensity of the light that locally impinges thereon is strong, it reduces the likelihood that a constraint will be encountered in terms of an upper limit on the dose of ultraviolet irradiation while ensuring that a higher level of safety will be achieved. This is described in further detail below.

There are cases where suppression of irradiative dose is sought where ultraviolet irradiation is employed in environments in which humans are present. For example, the ACGIH (American Conference of Governmental Industrial Hygienists) and JIS Z 8812 (Measuring Methods of Eye-Hazardous Ultraviolet Radiation) prescribe allowed limits (TLVs=threshold limit values) by wavelength for which the dose of ultraviolet irradiation that humans receive per day (8-hour period) should not be exceeded.

While as described above the wavelengths of emitted light used in accordance with the present invention are wavelengths for which the hazard to humans is extremely small, it is preferred to further increase safety that the dose of ultraviolet irradiation be set so as to satisfy the prescriptions of the aforementioned TLVs.

A large nonuniformity in emitted light indicates that there is a large difference in intensity between regions in which the intensity of light that locally impinges thereon is strong and regions in which the intensity of light that locally impinges thereon is weak. Where the dose of ultraviolet irradiation is to be set so as to satisfy the prescriptions of the aforementioned TLVs, it is preferred that the upper limit of the irradiative dose be set based on that which exists at the regions in which the intensity of light that locally impinges thereon is strong. When this is done, it will be the case that there will be an increased likelihood that a constraint will be encountered in terms of an upper limit of the dose of ultraviolet irradiation; and in particular, it will be the case that the dose of ultraviolet irradiation in regions in which the intensity of light that locally impinges thereon is weak will be limited more than is necessary.

Conversely, when nonuniformity in the emitted light is small, differences in light intensity from region to region will be small, and it will be less likely that a constraint will be encountered in terms of an upper limit on the dose of ultraviolet irradiation. Therefore, because the diffusing member 5 suppresses nonuniformity in the emitted light, the ultraviolet light irradiation device 10 reduces the likelihood that a constraint will be encountered in terms of an upper limit on the dose of ultraviolet irradiation while ensuring that a higher level of safety will be achieved.

To ensure that an even higher level of safety is achieved, the diffusing member 5 may be used to suppress the maximum local irradiance by ultraviolet light (the irradiance within that local region which is irradiated by light of the highest intensity). For example, the material, thickness, shape, and/or the like of the diffusing member may be chosen and/or adjusted so as to suppress the maximum local irradiance by ultraviolet light such that it is not greater than 3 mW/cm$^2$, or better yet not greater than 1 mW/cm$^2$, at the light-radiating surface of the diffusing member 5.

From the standpoint of causing inactivation of microorganisms as a result of irradiation with ultraviolet light, a diffusing member 5 that exhibits transmissivity with respect to ultraviolet light of wavelengths 190 nm to 235 nm may be employed. The diffusing member 5 may suppress transmission of ultraviolet light of wavelengths other than 190 nm to 235 nm.

The diffusing member 5 may provide diffusing effect not only with respect to ultraviolet light but also with respect to visible light. It may be assumed that the ultraviolet light irradiation device 10 described in the context of the present invention will be subject to application at a wide variety of sites and facilities. Were the excimer lamps 3, electrode blocks, and so forth at the interior of the ultraviolet light irradiation device 10 to become clearly identifiable, there is a possibility that this could impair the surrounding scenery or external appearance of the equipment. However, by causing a diffusing member that provides diffusing effect with respect to visible light to be arranged at the extracting portion 4, it will be possible to cause the excimer lamps 3 at the interior of the ultraviolet light irradiation device 10 to be made visually unperceivable or make it possible for them not to be seen clearly, as a result of which it will be possible to carry out inactivation of microorganisms while achieving harmonization with respect to the surrounding scenery and external appearance of the equipment.

The foregoing constitutes an overview of the diffusing member. Specific examples of diffusing members will be described below.

Optical Filter

Figure 6:
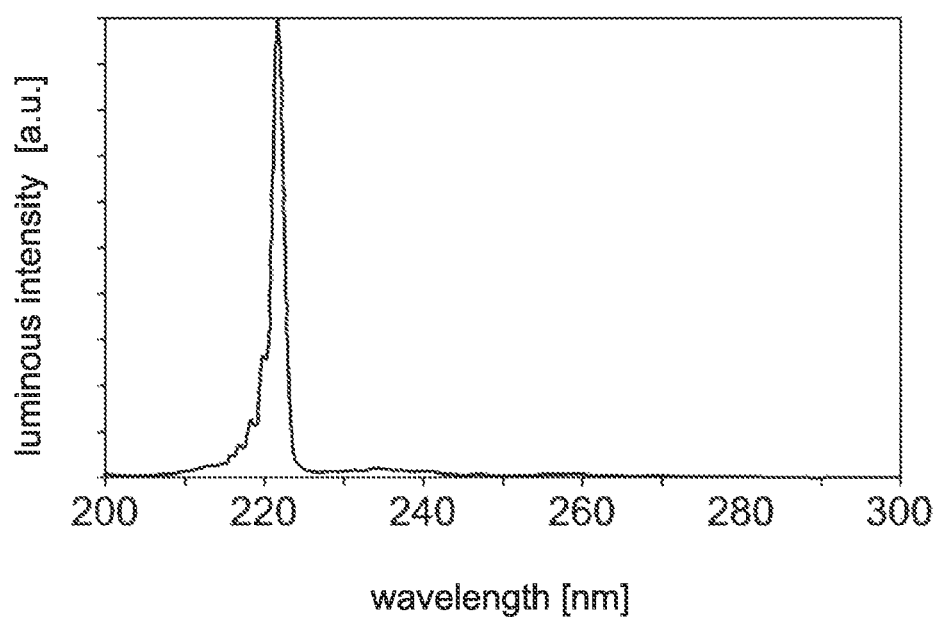
FIG. 6 Example of spectrum emitted by excimer lamp at which the light-emitting gas contains KrCl.

Optical filter 6 blocks, i.e., functions as a bandpass filter that substantially does not transmit, specific wavelength band(s) of ultraviolet light. For example, in the case of a KrCl excimer lamp, the spectrum of the ultraviolet light that is radiated therefrom is such that, as shown in FIG. 6, whereas the optical output is more or less concentrated in the vicinity of 222 nm, which is the primary peak wavelength, some small amount of optical output can also be discerned in the ultraviolet light wavelength band for which wavelength is not less than 240 nm and not greater than 280 nm, for which there is a possibility that there could be an effect on humans. In accordance with the present embodiment, an optical filter 6 is provided in a region constituting the extracting portion 4 so as to cause ultraviolet light of wavelength not less than 240 nm and not greater than 280 nm to be substantially not transmitted. By so doing, it will be possible by definitively suppressing leakage to the exterior of the housing of ultraviolet light in a wavelength band for which there is a possibility that there could be an effect on humans to further improve the safety of the light irradiation device for humans.

Furthermore, by causing ultraviolet light of not less than 240 nm and not greater than 300 nm to be substantially not transmitted, it will be possible to further improve the safety of the ultraviolet light irradiation device for humans. It being sufficient that the optical filter 6 be of such form as to function as a bandpass filter that blocks ultraviolet light of specific wavelength band(s), there is no limitation with respect to the manner in which it is embodied or the location at which it is arranged. For example, it may be formed such that it comes in contact with the light source, or it may be formed such that it is separated from the light source.

Throughout the present specification, to "substantially not transmit ultraviolet light" means that the intensity of ultraviolet light is at least suppressed so as to be not greater than 5% of the intensity of ultraviolet light at the peak wavelength within a specific wavelength band in the direction of the principal ray. In accordance with the present invention, employment of an optical filter makes it possible to block light such that the intensity of ultraviolet light of not less than 240 nm and not greater than 300 nm is not greater than 5% of the intensity at the peak wavelength. Moreover, it is preferred that the light within the wavelength band for which it is desired that light be blocked by the optical filter be suppressed to the point where the intensity of the ultraviolet light transmitted by the optical filter is not greater than 2% of the intensity at the peak wavelength. It is more preferred that this be suppressed to the point where the intensity of the ultraviolet light transmitted by the optical filter is not greater than 1% of the intensity at the peak wavelength.

There are optical filters 6 that are constituted so as to contain a plurality of dielectric multilayer films of differing refractive indices. Examples of dielectric multilayer films include those in which $HfO_2$ layers and $SiO_2$ layers are laminated in alternating fashion, and those in which $SiO_2$ layers and $Al_2O_3$ layers are laminated in alternating fashion. Because they permit decrease in the number of layers necessary to obtain the same wavelength selection properties, dielectric multilayer film layers in which $HfO_2$ layers and $SiO_2$ layers are laminated in alternating fashion will, more than dielectric multilayer film layers in which $SiO_2$ layers and $Al_2O_3$ layers are laminated in alternating fashion, make it possible to increase the transmittance of the selected ultraviolet light.

While as described above there are optical filters 6 that are constituted so as to contain a plurality of dielectric multilayer films of differing refractive indices, there is no avoiding the fact that the transmittance of an optical filter 6 which is made up of dielectric multilayer films will vary depending on the angle of incidence of ultraviolet light.

Figure 7:
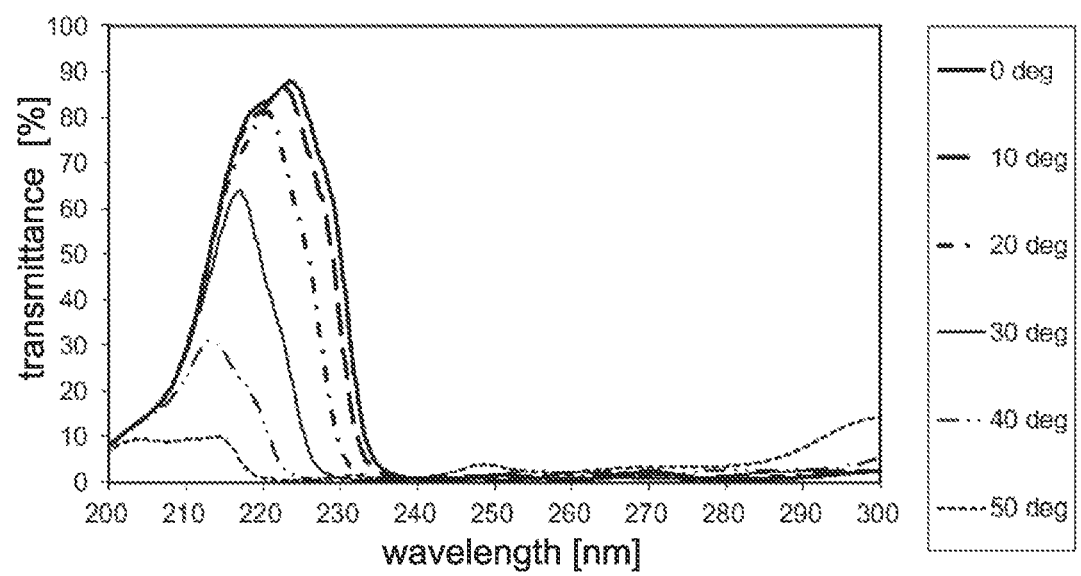
FIG. 7 Graph showing exemplary transmission spectra at an optical filter.
Figure 8:
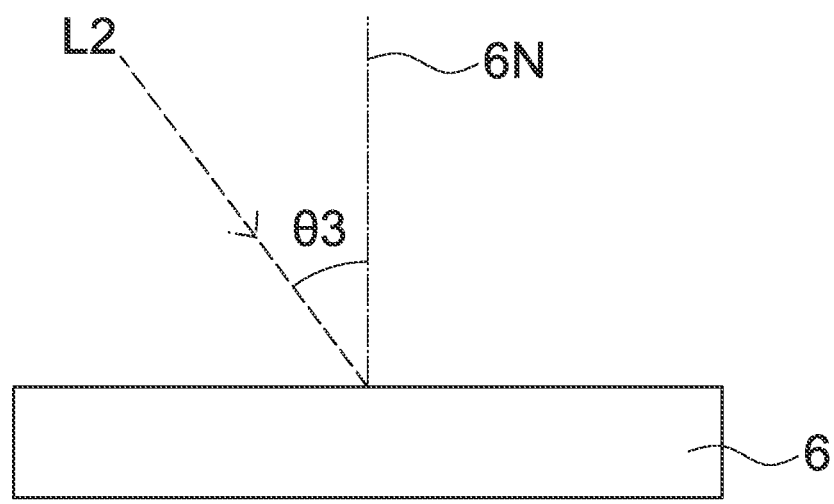
FIG. 8 Schematic diagram for explaining the angle of incidence of ultraviolet light on an optical filter.

FIG. 7 is a graph showing exemplary transmission spectra at an optical filter 6 when ultraviolet light of different angles of incidence are incident on the optical filter 6. The exemplary situation shown in this graph is predicated on a design for an optical filter 6 in a situation in which a light-emitting gas at the excimer lamps 3 contains KrCl; i.e., a situation in which ultraviolet light having a primary peak wavelength of 222 nm is emitted by the excimer lamps 3. The respective curves in the graph were obtained by plotting the ratio of the intensity of light emitted from the optical filter 6 to the intensity of light incident on the optical filter 6 while varying wavelength. As shown in FIG. 8, the angle of incidence is defined as the angle θ3 between the ultraviolet light L2 incident on the plane of incidence of the optical filter 6 and a line 6N normal to the plane of incidence of the optical filter 6.

From the graph in FIG. 7, it is clear that the optical filter 6 tends to transmit optical components having small angles of incidence (angle θ3) but tends not to transmit optical components having large angles of incidence. Optical components having large angles of incidence do not proceed through the optical filter 6 but are reflected. As a result, the relative percentage of optical components having small angles of incidence is higher, and the angular divergence thereof is smaller, at the light that exits the optical filter 6 than it is at the light that is incident on the optical filter 6. To put it another way, the optical filter 6 decreases the angular divergence of the light.

Based on this state of affairs, especially remarkable benefit can be obtained by the aforementioned diffusing member 5 when an optical filter 6 that decreases the angular divergence is employed. This is to say that even where an optical filter 6 is used and the angular divergence is decreased thereby, it will still be possible to obtain a large angular divergence from the ultraviolet light irradiation device 10 by causing the diffusing member 5 to be arranged downstream from the optical filter 6 (i.e., by causing the optical filter 6 to be arranged between the excimer lamps 3 and the diffusing member 5). Note, however, that the optical filter 6 is not essential to the constitution of the ultraviolet light irradiation device 10.

Figure 9:
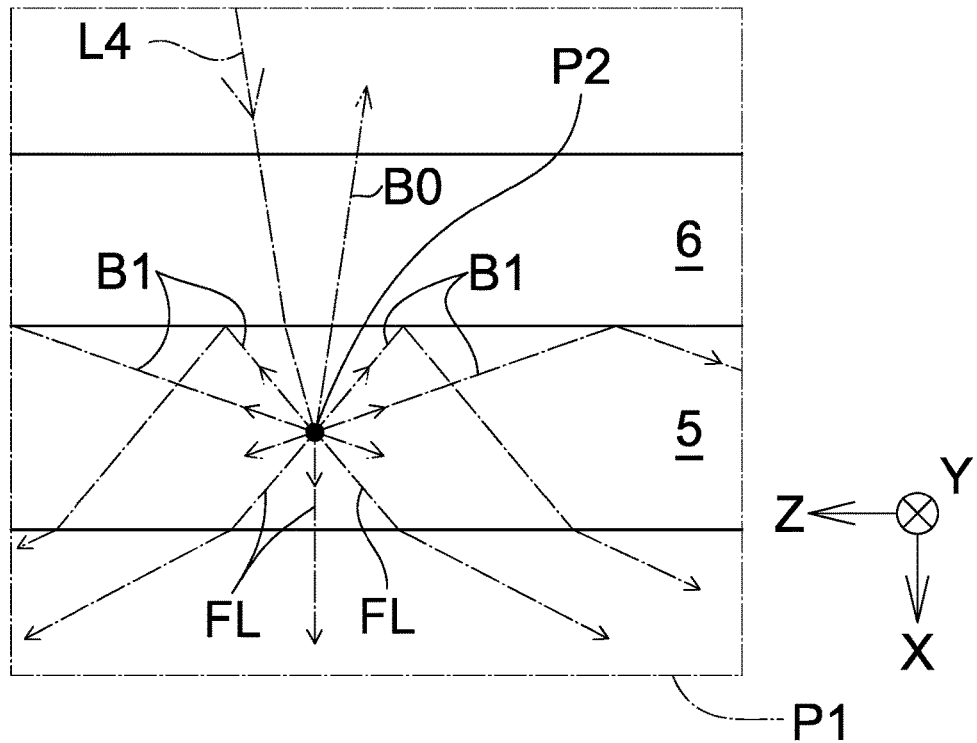
FIG. 9 Enlarged view of region P1 at FIG. 4.

A further benefit of using the diffusing member 5 in combination with an optical filter 6 is the reflection effect pertaining to the light that is reflected backward by the diffusing member 5 at the optical filter 6. This will be described with reference to FIG. 9. FIG. 9 is an enlarged view of region P1 in FIG. 4. When considered from a microscopic perspective, the effect by which light L4 incident on a point P2 at the diffusing member 5 is diffused is such that the light L4 is diffused in various directions at the point P2.

Whereas light FL that is refracted at the point P2 such that it proceeds in the +X direction exits the ultraviolet light irradiation device 10, light (B0, B1) that is diffused at the point P2 such that it proceeds in the −X direction is backwardly reflected light that tends to return to the interior of the housing of the ultraviolet light irradiation device 10.

However, as has been described above, the optical filter 6 has a property by which it tends to transmit optical components having small angles of incidence but reflect optical components having large angles of incidence. For this reason, of the light that is backwardly reflected from the point P2, the majority B1 of that light has a large angle of incidence on the optical filter 6 and will be changed into light that proceeds in the +X direction. Backwardly reflected light that returns as far as the interior of the housing will have a small angle of incidence on the optical filter 6 and will be only a small amount B0 of light. It will therefore be possible to suppress the backwardly reflected light that returns as far as the interior of the housing and to improve optical output efficiency.

Based on the foregoing, whereas a diffusing member 5 is provided for the purpose of attaining the benefit of increasing the angular divergence of the light at an optical filter 6 which is arranged thereat for the purpose of wavelength selection, when one looks at the optical filter 6 one sees that it makes it possible to also attain a benefit whereby backwardly reflected light produced as a result of provision of the diffusing member 5 is suppressed. Use of a diffusing member 5 in combination with an optical filter 6 will make it possible to simultaneously attain these two different benefits.

Causing the diffusing member 5 to be arranged so as to come in contact with the optical filter 6 will make it possible to increase the angle of incidence on the optical filter 6 of the light that is backwardly reflected by the diffusing member 5 more than would be the case where the diffusing member 5 arranged so as to be separated from the optical filter 6. By causing the diffusing member 5 to be arranged so as to come in contact with the optical filter 6, it will therefore be possible to suppress the backwardly reflected light and to further improve optical output efficiency.

Specific Examples of Diffusing Members

There being no particular limitation with respect to the shape or thickness of the diffusing member 5, it may be film-like or it may be plate-like, for example. The diffusing member 5 might, for example, be formed by causing fine surface irregularities to be provided on the surface of a base material that transmits ultraviolet light or by causing there to be mixed presence of substances of differing refractive indices and/or voids at the interior of a base material that transmits ultraviolet light. The fine surface irregularities may be formed by employing etching or shot/sand blasting to cause partial ablation of the surface of the base material, or may be formed by causing partial addition (or printing) of resin or other such particles on the surface of the base material.

The material of the diffusing member 5 might, for example, employ polycarbonate, polyethylene, PET or other such resin, or PTFE, PFA, PVDF, or other such fluororesin as primary material, or it might employ quartz glass or other such glass as primary material. Based on the fact that PTFE and quartz glass tend not to degrade over time, they are particularly superior as materials for the diffusing member 5.

Figure 10A:
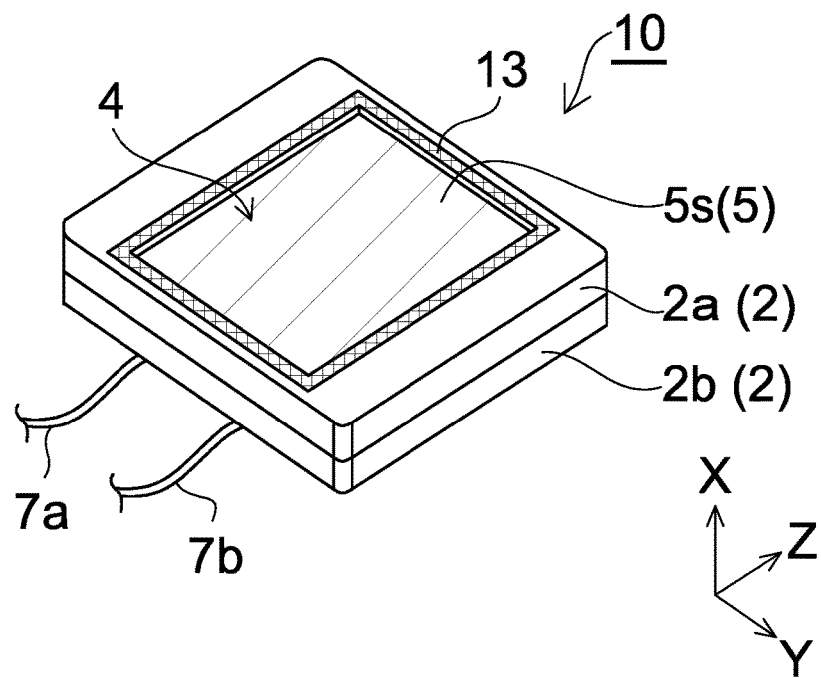
FIG. 10A Perspective view showing in schematic fashion the external appearance of an ultraviolet light irradiation device having a diffusing member in accordance with a first example.
Figure 10B:
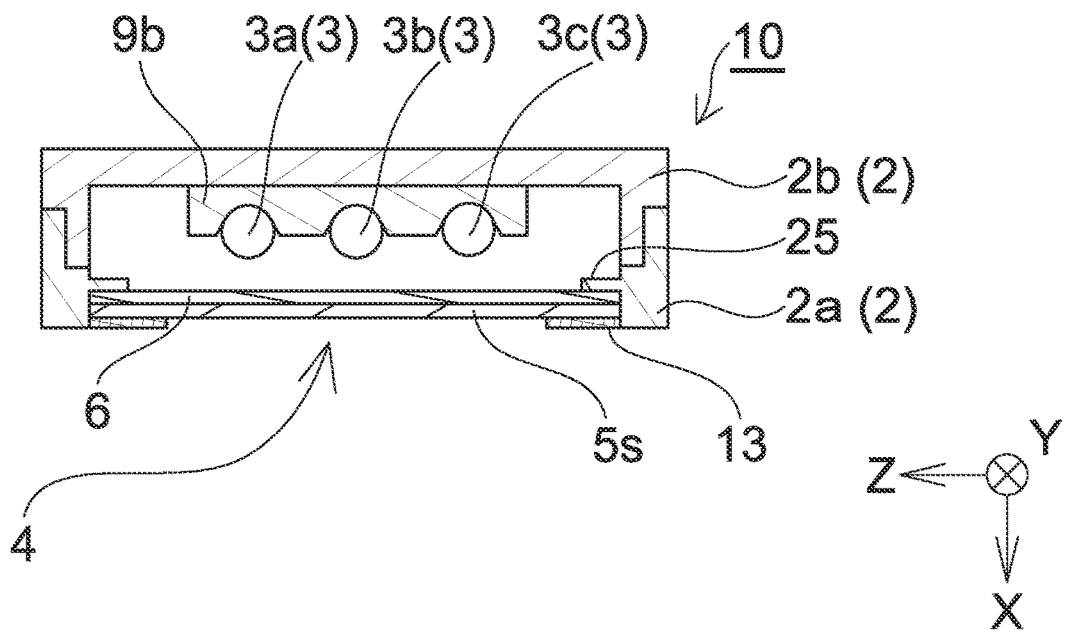
FIG. 10B Sectional schematic view of the ultraviolet light irradiation device at FIG. 10A.

A first example of a diffusing member 5 will be described with reference to FIG. 10A and FIG. 10B. FIG. 10A is a perspective view showing in schematic fashion the external appearance of an ultraviolet light irradiation device 10, and FIG. 10B is a sectional schematic view of the XZ plane at the ultraviolet light irradiation device 10. At the ultraviolet light irradiation device 10, a diffusing member 5 is constituted so as to include a diffusing sheet 5s. The ultraviolet light irradiation device 10 has a securing portion 13 that secures the diffusing sheet 5s.

In accordance with the present embodiment, a diffusing sheet (hereinafter sometimes referred to as "PTFE sheet") that primarily employs PTFE (polytetrafluoroethylene) as primary constituent is used as the diffusing sheet 5s. Because PTFE is such that the molecular structure thereof itself possesses crystallinity which exhibits diffusion of light, it is suitable for use as a diffusing member. Note that what is referred to as a primary constituent is that constituent which is most abundant within the diffusing sheet. The primary constituent may constitute not less than 90 mass % of the content of the diffusing sheet, or it may constitute not less than 95 mass % of the content of the diffusing sheet.

Methods for manufacturing PTFE sheets include methods in which PTFE microparticles are sintered in the shape of a sheet, methods in which a base material on which PTFE microparticles have been compacted is stretched into the shape of a sheet, and so forth. Thereamong, where a PTFE sheet is manufactured using a method in which PTFE microparticles are sintered in the shape of a sheet, because this will cause a porous structure to be exhibited in which many gaps are formed between microparticles, and because the porous structure will diffuse an especially large amount of light, the light diffusing properties thereof will be particularly superior. Furthermore, when PTFE microparticles are sintered in the shape of a sheet, the crystallinity of the PTFE will differ depending on the sintering temperature. A high sintering temperature will increase the crystallinity of the PTFE sheet and will increase the diffusivity thereof.

As diffusing sheet materials other than PTFE, materials employing another fluororesin such as PFA or PVDF, or polycarbonate, polyethylene, PET or other such resin, as primary material may be used. It is preferred that thickness of the diffusing sheet be less than 1 mm, and more preferred that this be less than 0.5 mm.

The securing portion 13 exhibits a frame-like shape that encloses the periphery of the extracting portion 4. The diffusing sheet 5s is secured in such fashion that it is interposed by the optical filter 6 and the securing portion 13. The optical filter 6 is supported in the X direction by a protruding portion 25 that protrudes from an inside wall of a first frame 2a. By causing the diffusing sheet 5s to be secured in this fashion, the diffusing sheet 5s is arranged so as to come in contact with the optical filter 6, permitting the diffusing sheet 5s to be easily supported even where the diffusing sheet 5s is thin. The frame-like securing portion 13 may be made up of material that transmits ultraviolet light, or may be made up of material that does not transmit ultraviolet light (e.g., metal, resin, or the like).

An adhesive may be used to secure the diffusing sheet 5s. But where adhesive is used at a location that is exposed to ultraviolet light, note that there is a possibility this will cause occurrence of a problem in which the ultraviolet light causes the adhesive to degrade. Where a securing portion 13 is used to secure the diffusing sheet 5s in interposed fashion without use of adhesive, such problems will not occur.

Figure 11:
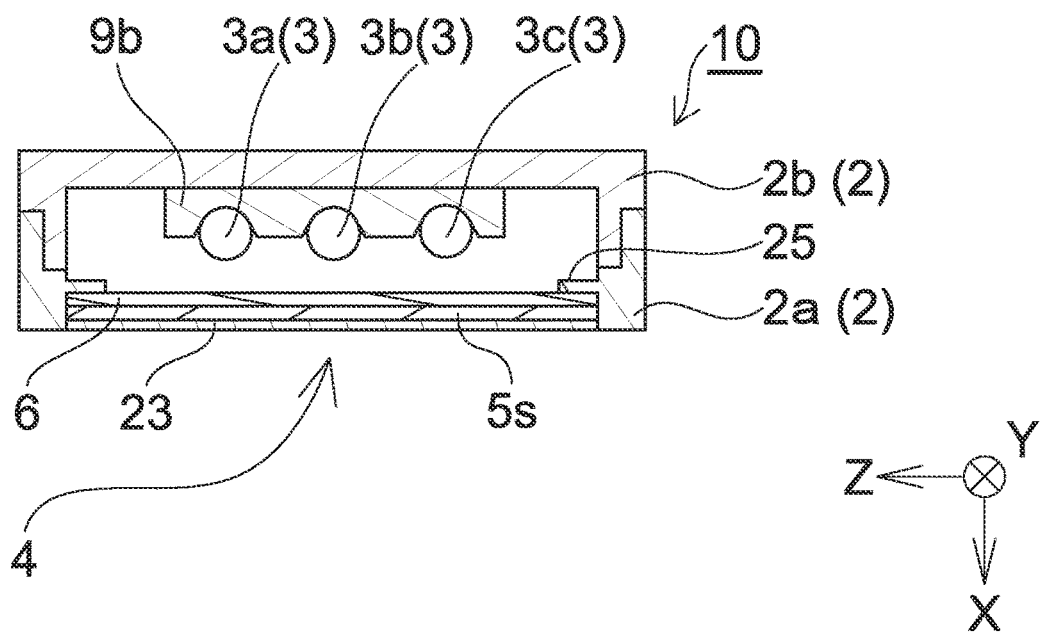
FIG. 11 Drawing showing a variation on a securing portion that secures a diffusing member.

FIG. 11 shows a variation on the securing portion for securing the diffusing member. The securing portion 23 shown in FIG. 11 is a transmissive plate that transmits ultraviolet light. The diffusing sheet 5s is secured in such fashion that it is interposed by the optical filter 6 and the securing portion 23 which is a transmissive plate. The transmissive plate might employ quartz glass, for example. As another variation thereon, a mesh-like member that covers the diffusing sheet 5s may be used to secure the diffusing sheet 5s. The mesh-like member may employ a material that does not transmit ultraviolet light (e.g., metal, resin, or the like). At FIG. 11, the securing portion 23 is provided in such fashion as to cover the extracting portion 4.

Figure 12A:
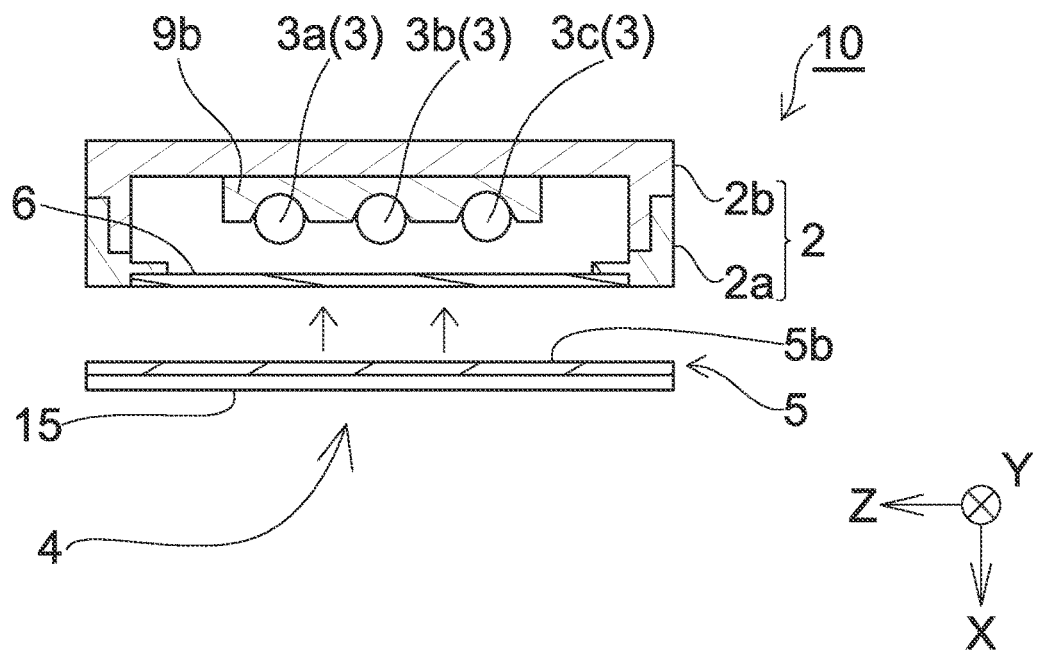
FIG. 12A Sectional schematic view of an ultraviolet light irradiation device having a diffusing member in accordance with a second example.

A second example of a diffusing member 5 will be described with reference to FIG. 12A. While for purposes of description FIG. 12A shows the ultraviolet light irradiation device 10 in a state in which it is separated into a housing 2 and a diffusing member 5, note that in reality the diffusing member 5 would be arranged so as to come in contact with the housing 2 or so as to be in the vicinity of the housing 2. The ultraviolet light irradiation device 10 has a diffusing member 5 which is constituted so as to include a diffusing film 5b. At FIG. 12A, the diffusing film 5b is formed on one principal plane of quartz glass 15 which serves as substrate. The ultraviolet light irradiation device 10 is such that the quartz glass 15 together with the diffusing film 5b which is formed thereon is attached to the housing 2. When attaching the quartz glass 15 to the housing 2, this may be done such that the diffusing film 5b and the optical filter 6 are mutually separated, or such that they are in mutual contact.

The diffusing film 5b might, for example, be a material in which silica or alumina is primary constituent. It is preferred that thickness of the diffusing film be less than 1 mm, and more preferred that this be less than 0.5 mm.

Exemplary description of a method for forming diffusing film 5b will be given in terms of an example employing a silica diffusing film. Milled silica that has been heated and melted under atmospheric conditions might be sprayed onto the surface of quartz glass 15 (thermal spraying method). The milled silica might, for example, be microparticles that are more or less spherical in shape and have a particle diameter of 100 nm to 100 μm. Bonding agent for bonding the microparticles may be sprayed together with the microparticles. Other film forming method(s)—e.g., sprayed application without employment of heating, immersion coating, spin coating, and/or the like—may be employed.

Figure 12B:
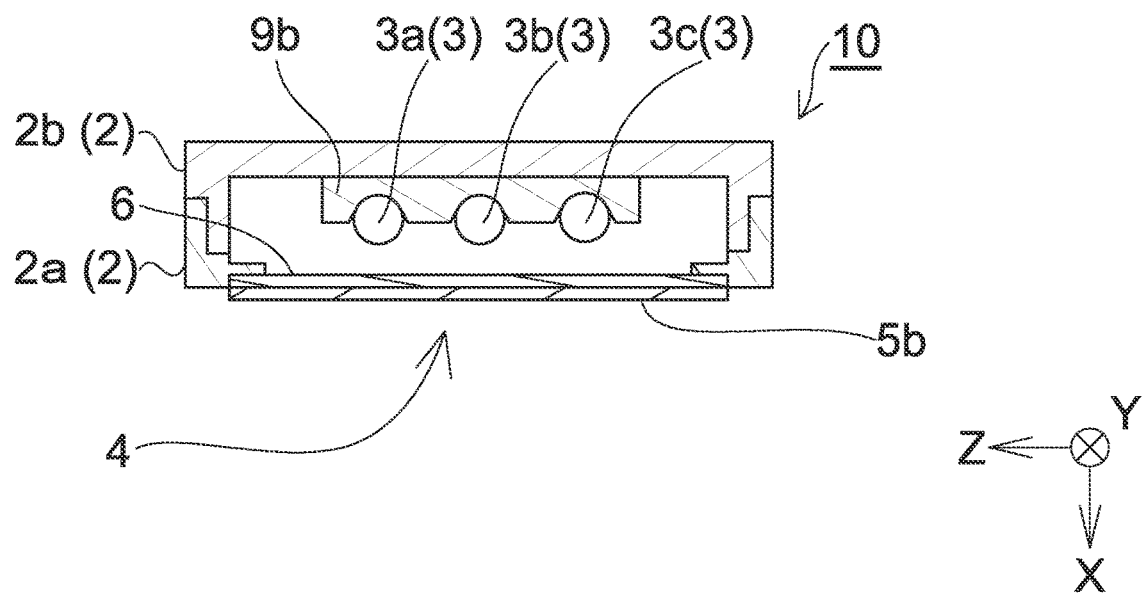
FIG. 12B Sectional schematic view of an ultraviolet light irradiation device having a diffusing film formed on an optical filter.

FIG. 12B is a variation on a diffusing member 5 which is constituted so as to include a diffusing film 5b. At the variation, the diffusing film 5b is formed directly on the optical filter 6.

Method of Use

As a manner of using an ultraviolet light irradiation device associated with the present invention, the ultraviolet light irradiation device may be arranged such that irradiation by the ultraviolet light that exits therefrom will be directed toward a space used by humans, and this may be made to irradiate ultraviolet light. A space used by humans means a space that human(s) are capable of entering, regardless of whether or not humans are actually present therein. Spaces used by humans might, for example, include spaces within homes, offices, schools, hospitals, theatres, and other such buildings; and might, for example, include spaces within automobiles, buses, trains, airplanes, and other such modes of transportation. The ultraviolet light irradiation device 10 might be arranged at a ceiling, wall, pillar, floor, or the like that faces a space used by humans and in such fashion as to cause the extracting portion 4 to be directed toward the space used by humans. In addition, the ultraviolet light irradiation device 10 might be turned on, causing the ultraviolet light that is irradiated therefrom to be directed toward the space used by humans.

In accordance with this method of use, there being no need to cause irradiation by ultraviolet light to occur in such fashion that humans are avoided as had been the case conventionally, it will be possible to cause ultraviolet light to, entirely and without nonuniformity (with little nonuniformity), irradiate spaces used by humans, including surfaces (skin and/or the like) of humans, surfaces of objects with which people frequently come in contact, and spaces around humans, these being vital places at which inactivation of microorganisms is most in need of being carried out. For this reason, it will be possible to carry out effective inactivation of microorganisms.

The foregoing ultraviolet light irradiation device may be built into fluorescent lamps, LEDs, and other such lighting equipment. Where this is to be built into lighting equipment, the foregoing diffusing member used by the ultraviolet light irradiation device may also serve as a visible light diffusing member used by the lighting equipment.

Second Embodiment

Figure 13:
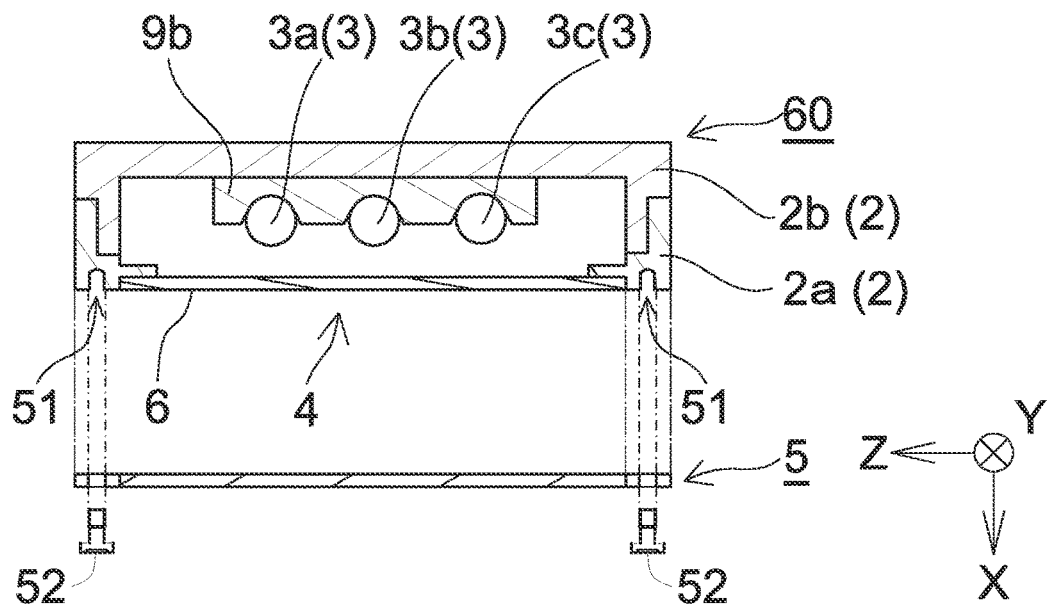
FIG. 13 Drawing for explaining a second embodiment of an ultraviolet light irradiation device.

A second embodiment of a light irradiation device in accordance with the present invention will be described with reference to FIG. 13. Items other than those described below may be implemented in similar fashion as at the first embodiment. An ultraviolet light irradiation device 60 in accordance with the second embodiment is provided with excimer lamps 3 (3a, 3b, 3c), a housing 2, an extracting portion 4 that extracts the ultraviolet light which is radiated from the excimer lamps 3 and causes it to be directed toward the exterior of the housing 2, and an optical filter 6 that is disposed at the extracting portion 4 and that transmits ultraviolet light within a wavelength band of 190 nm to 235 nm but substantially does not transmit ultraviolet light within a wavelength band of 240 nm to 280 nm or less.

The ultraviolet light irradiation device 60 of the present embodiment is not provided with a diffusing member 5. The housing 2 has an attachment portion 51 for attachment of a diffusing member 5 so as to permit a diffusing member 5 to be attached to the ultraviolet light irradiation device 60 at a later time. In accordance with the present embodiment, the attachment portion 51 is a threaded hole, it being possible to attach a diffusing member 5 to the ultraviolet light irradiation device 60 by causing a screw 52 to engage with the threaded hole such that the diffusing member 5 is interposed thereby. This attachment portion 51 for the diffusing member 5 is an exemplary mode, it also being possible to employ hook(s), surface fastener(s), and/or any other(s) among various possible modes. Causing the diffusing member 5 to be made capable of being attached at a later time will make it possible for only the diffusing member 5 to be replaced should the diffusing member 5 be subject to degradation.

While embodiments of ultraviolet light irradiation devices and methods of using ultraviolet light irradiation devices have been described above, the present invention is not to be limited in any way by the foregoing embodiments, a great many variations and/or improvements on the foregoing embodiments being possible without departing from the gist of the present invention.

For example, whereas description was given in terms of an example in which excimer lamp(s) 3 were employed as light source, a solid state light source constituted from LD(s) and/or LED(s) may be employed as light source.

For example, a light source that radiates ultraviolet light having a primary emission wavelength of 190 nm to 230 nm may be employed. Employment of ultraviolet light for which the upper limit of the range in values for the primary emission wavelength is 230 nm will more than employment of ultraviolet light for which the upper limit of the range in values for the primary emission wavelength is 235 nm permit further increase in safety for humans.

For example, a light source that radiates ultraviolet light having a primary emission wavelength of 200 nm to 230 nm may be employed. Ultraviolet light for which the lower limit of the range in values for the primary emission wavelength is 200 nm will have poorer ability to cause decomposition of oxygen in the atmosphere and production of ozone than ultraviolet light for which the lower limit of the range in values for the primary emission wavelength is 190 nm. Because gases having high concentrations of ozone present a hazard to humans, suppression of production of ozone will permit further increase in safety for humans. Furthermore, the foregoing wavelength bands need not be those of a primary emission wavelength.

For example, an optical filter that transmits ultraviolet light within a wavelength band of 200 nm to 230 nm but substantially transmits neither ultraviolet light within a wavelength band of 240 nm to 280 nm nor ultraviolet light within a wavelength band below 200 nm may be employed as the optical filter. By causing ultraviolet light within a wavelength band below 200 nm to be substantially not transmitted, it will be possible to suppress production of ozone and further increase safety for humans.

For example, a reflecting member that reflects light radiated by the light source may be arranged within the housing 2. By causing a reflecting member to be arranged thereat, it will be possible to reduce the amount of light that is directed toward the inside wall of the housing 2 from the light source, to increase the amount of light that is directed toward the extracting portion 4, and to increase the irradiance of the light that exits the ultraviolet light irradiation device 10.

The diffusing member 5 and/or the optical filter 6 may be arranged not only at the opening of the housing 2 that constitutes the extracting portion 4 but may also be arranged so as to be located outside the housing 2.

Improvement of Optical Output Efficiency

As improvements on the foregoing embodiments, the optical output efficiency may be improved. Among such an improvement, e.g., as an example of a reflecting member, a film of a material exhibiting reflectivity with respect to ultraviolet light may be formed at the electrode blocks (9a, 9b), and/or the foregoing electrode blocks (9a, 9b) may themselves be constituted from a material exhibiting reflectivity with respect to ultraviolet light. If the surfaces of the electrode blocks (9a, 9b) are made to exhibit reflectivity, the electrode blocks (9a, 9b) will also function as a reflector for causing the ultraviolet light to be directed toward the extracting portion 4. Furthermore, while described in further detail below, a reflector which is a different structure than the electrode blocks (9a, 9b) may be provided for causing even more light to be directed toward the extracting portion 4.

While as has been described above there are optical filters 6 that are constituted so as to contain a plurality of dielectric multilayer films of differing refractive indices, the transmittance and reflectance of an optical filter 6 which is made up of dielectric multilayer films will vary depending on the angle of incidence of ultraviolet light. For example, as shown in the graph of FIG. 7, it is clear that optical components having small angles of incidence tend to be transmitted but optical components having large angles of incidence tend not to be transmitted. As shown in FIG. 8, what is referred to here as an angle of incidence is defined as the angle θ3 between the ultraviolet light L2 incident on the plane of incidence of the optical filter 6 and a line 6N normal to the plane of incidence of the optical filter 6.

Based on such state of affairs, for ultraviolet light that is incident on the optical filter 6 at a comparatively large angle of incidence (e.g., not less than) 30°, the transmittance of the optical filter 6 will be poor, and the optical output efficiency of the optical filter 6 will be no better than a given level. Furthermore, a portion of the light that is reflected by the optical filter 6 irradiates the housing (casing) 2, as a result of which there is a possibility that the housing 2 will experience degradation. For this reason, it is preferred that the ultraviolet light that is radiated from the light source be made such that the rays of light therein are controlled so as to cause the angle of incidence when incident on the optical filter 6 to be small. This is particularly preferred when the light source and the optical filter 6 are arranged so as to be separated.

It is therefore preferred that the ultraviolet light irradiation device increase the directionality of ultraviolet light radiated from the light source and be provided with optical element(s) such as will increase optical components having small angles of incidence on the optical filter 6. By increasing optical components having small angles of incidence and reducing optical components having large angles of incidence on the optical filter 6, this will make it possible to increase the optical output efficiency of the optical filter 6. Optical lens(es), optical film(s), reflector(s), and/or the like such as will permit control so as to cause the directionality of ultraviolet light radiated from the light source to be increased and the angle of incidence on the optical filter 6 to be made small may be employed as the aforementioned optical element(s).

Optical Element(s)

Figure 14:
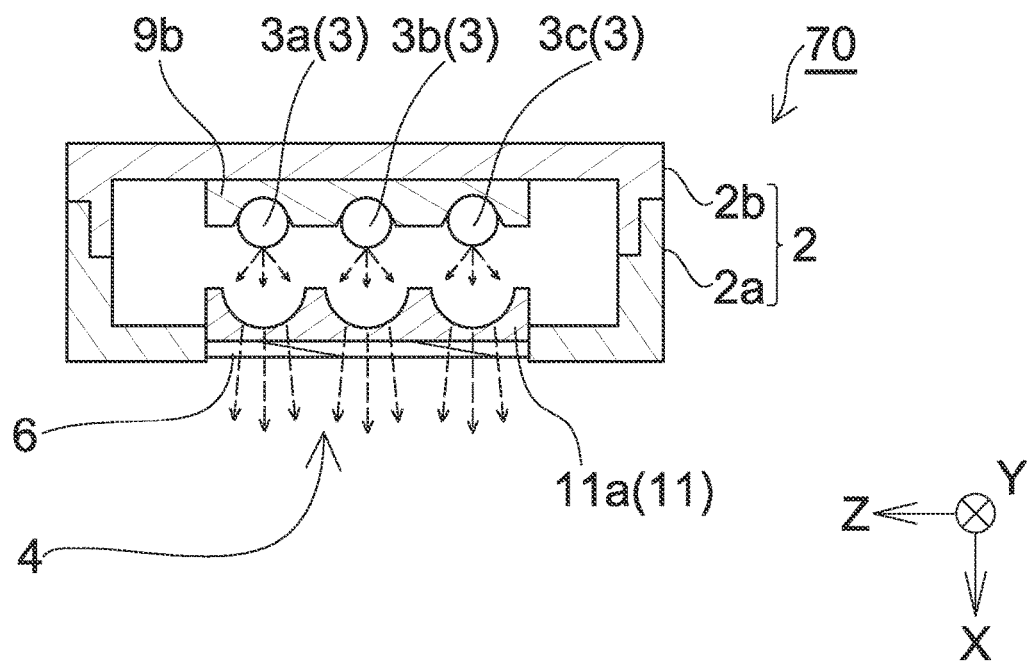
FIG. 14 Sectional schematic view of an ultraviolet light irradiation device provided with an optical lens.

An embodiment of an optical element will be described with reference to FIG. 14. FIG. 14 shows a sectional schematic view of an ultraviolet light irradiation device 70 that employs optical lenses 11a as optical elements 11. The optical lenses 11a are condensing lenses that reduce the angular divergence of ultraviolet light radiated from the light source. Ultraviolet light for which angular divergence has been reduced by the condensing lenses will be more readily made incident on the optical filter.

The optical lenses 11a are arranged between the light source (excimer lamps 3 in the present case) and the optical filter 6. It is sufficient that the optical lenses 11a reduce the angular divergence of ultraviolet light radiated from the light source, there being no particular limitation with respect to the shapes thereof. Furthermore, while FIG. 14 shows control to reduce the angle of incidence as manifested in a section taken along the XZ plane, control to reduce the angle of incidence as manifested in a section taken along the XY plane may be carried out. Furthermore, control to reduce the angle of incidence as manifested in both a section taken along the XZ plane and a section taken along the XY plane may be carried out.

Figure 15:
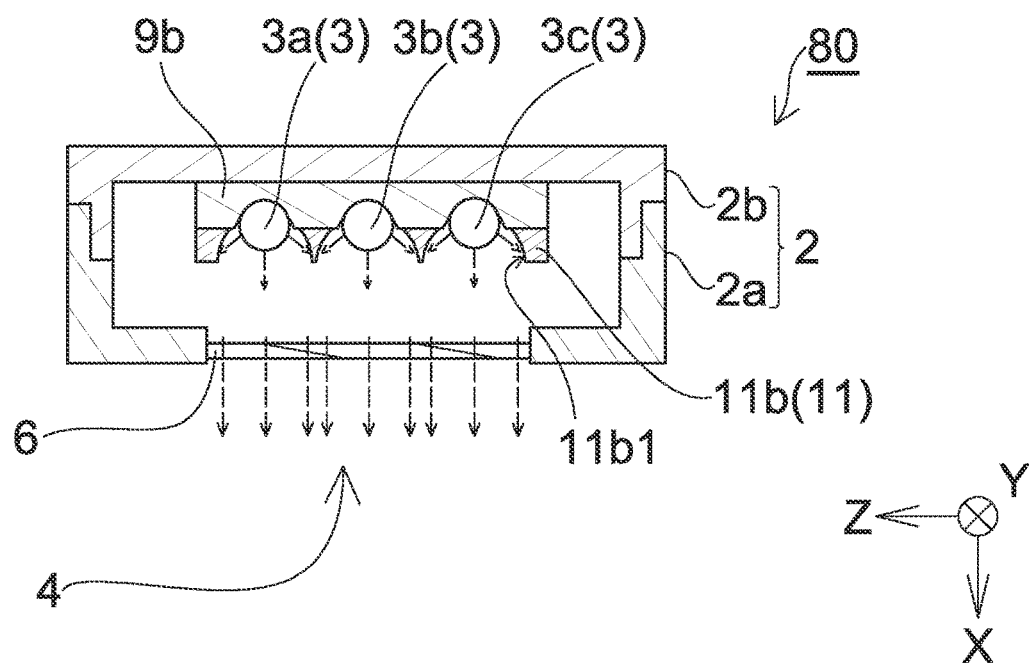
FIG. 15 Sectional schematic view of an ultraviolet light irradiation device provided with a reflector.

Another embodiment of an optical element will be described with reference to FIG. 15. FIG. 15 shows a sectional schematic view of an ultraviolet light irradiation device 80 that employs reflectors 11*b* as optical elements 11.

Ultraviolet light irradiation device 80 is such that provided in the vicinity of at least one of the electrode blocks (9*a*, 9*b*) is/are reflector(s) 11*b* which serve as optical element(s) 7. FIG. 15 shows an example in which reflector(s) 11*b* are provided at the electrode block 9*b*.

The reflector 11*b* may be provided with reflecting surface(s) 11*b*1 that is/are curved and/or planar so as to be inclined with respect to an extracting portion 4 equipped with an optical filter 6. The reflecting surface 11*b*1 is shaped such that the width of the opening thereof increases toward the optical filter 6. At FIG. 15, the reflector 11*b* is such that a reflector 11*b* that tapers so as to narrow toward the optical filter 6 is provided, a reflecting surface 11*b*1 being provided at the side face of the tapered portion thereof. Whereas the reflecting surface 11*b*1 is curved, it may also be formed so as to be planar.

At the reflector 11*b*, presence of reflecting surface(s) 11*b*1 that is/are curved and/or planar so as to be inclined with respect to a light-extracting surface causes a portion of the ultraviolet light irradiated from the light source (excimer lamps 3 in the present case) to be reflected by the reflecting surface(s) 11*b*1 such that the direction of travel thereof is altered. Describing this in further detail, of the ultraviolet light that is radiated from the light source with a given angular divergence, that ultraviolet light which proceeds therefrom with a large angular divergence is reflected by the reflecting surface(s) 11*b*1 such that the direction(s) in which it proceeds is/are altered. Because the reflecting surface 11*b*1 is constituted from curved surface(s) and/or planar surface(s) inclined with respect to the optical filter 6, following reflection thereof by the reflecting surface 11*b*1, the angle of incidence thereof when incident on the optical filter is reduced. By thus increasing optical components having small angles of incidence and reducing optical components having large angles of incidence on the optical filter 6, this will make it possible to increase the optical output efficiency of the optical filter 6. In particular with regard to the reflecting surface 11*b*1, by causing this to be in the shape of a parabolically curved surface, it will be possible to cause the angular divergence from the light source to be made to have better directionality, and it will be possible to increase the output efficiency of the optical filter 6.

Whereas at FIG. 15 the reflector 11*b* is constituted so as to be a different structure than the electrode blocks, the reflector 11*b* and the electrode blocks may be formed in integral fashion. In such case, reflector(s) 11*b* would be formed at at least one of the electrode blocks (9*a*, 9*b*).

It is preferred that the electrode blocks (9*a*, 9*b*) and the reflector(s) 11*b* be constituted from material(s) (e.g., Al, Al alloy, stainless steel, and/or the like) exhibiting reflectivity with respect to ultraviolet light with a wavelength in a range of 190 nm to 235 nm. Because this will make it possible for ultraviolet light radiated from the light source (excimer lamps 3 in the present case) to be reflected by the electrode blocks (9*a*, 9*b*) and by the reflector 11*b*, this will make it possible to improve optical output efficiency. For example, the respective electrode blocks (9*a*, 9*b*) may be such that a first surface which is curved and which comes in contact with the outer surfaces of the light-emitting tubes of the respective excimer lamps 3 (3*a*, 3*b*, 3*c*) and a second surface which is curved and which is inclined with respect to the light-extracting surface are made to be of mutually continuous shape, ultraviolet light radiated from the excimer lamps 3 being reflected by the first surface and the second surface. In other words, supply of electricity may be carried out at the first surface which comes in contact with the outer surfaces of the light-emitting tubes, and ultraviolet light may be reflected at the first surface and the second surface, permitting increase in optical components having small angles of incidence on the optical filter 6. The first surface and the second surface would be constituted from respectively different curved shapes.

At FIG. 14 and FIG. 15, optical element(s) 11 are provided at the interior of the housing 2. Ultraviolet light radiated from the light source is incident on the optical filter 6 by way of the optical element(s) 11, increasing optical components for which the angle of incidence of ultraviolet light on the optical filter 6 is small.

With respect to the improvement of optical output efficiency that results from the fact that the angle of incidence on the optical filter 6 is made small, because from the standpoint of the ultraviolet light irradiation device the diffusing member may be of any desired constitution, a diffusing member is not shown in FIG. 14 or FIG. 15. However, the ultraviolet light irradiation devices (70, 80) shown in FIG. 14 and FIG. 15 may also be further provided with a diffusing member that diffuses the ultraviolet light that exits the optical filter 6. This will make it possible to increase the optical output efficiency of the optical filter 6, and will also make it possible to increase the angular divergence of the ultraviolet light by means of the diffusing member.

WORKING EXAMPLES

Figure 16:
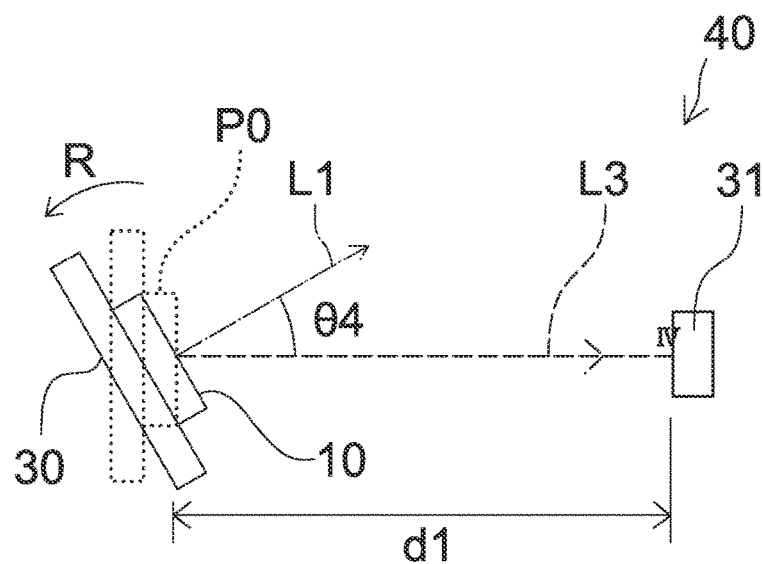
FIG. 16 Drawing showing in schematic fashion measuring equipment for measuring the action of a diffusing member.

The effect by which angular divergence may be increased through use of a diffusing member 5 was determined for the ultraviolet light irradiation device 10 presented at the foregoing embodiments. The ultraviolet light irradiation device 10 is described in further detail below. FIG. 16 shows measuring equipment 40 for measuring the angular divergence of an ultraviolet light irradiation device 10. The measuring equipment 40 includes the ultraviolet light irradiation device 10, a rotary stage 30 on which the ultraviolet light irradiation device 10 is placed, and an irradiance meter 31. Note that a C8026 UV Power Meter manufactured by Hamamatsu Photonics K.K. was used as the irradiance meter 31.

The measuring equipment 40 included the rotary stage 30, the ultraviolet light irradiation device 10 which was placed on the rotary stage 30, and the irradiance meter 31 which was arranged at a location separated by a distance d1 (mm) from the ultraviolet light irradiation device 10. The position of the rotary stage 30 when the ultraviolet light irradiation device 10 was arranged in opposing fashion with respect to the irradiance meter 31 such that the irradiance meter 31 was located on the optical axis L1 of the ultraviolet light irradiation device 10 was taken to be the initial position P0 thereof. The rotary stage 30 was rotated in the rotational direction R shown in FIG. 16 from the initial position P0. At FIG. 16, the ultraviolet light irradiation device 10 and the rotary stage 30 as they existed when at the initial position P0 are shown in broken line, and the ultraviolet light irradiation device 10 and the rotary stage 30 as they existed following rotation for a prescribed time in the rotational direction R are shown in solid line.

The angle θ4 between the optical axis L1 of the ultraviolet light irradiation device 10 and a ray L3 incident on the irradiance meter 31 from the ultraviolet light irradiation device 10 represents the rotational angle. While the ultraviolet light irradiation device 10 was made to irradiate the ultraviolet light, the irradiance meter 31 was used to measure irradiance as the rotational angle θ4 was increased (the rotary stage 30 was rotated) from the initial position P0 at which the rotational angle θ4 was 0° (deg) until the rotational angle θ4 was 90° (deg).

Figure 17A:
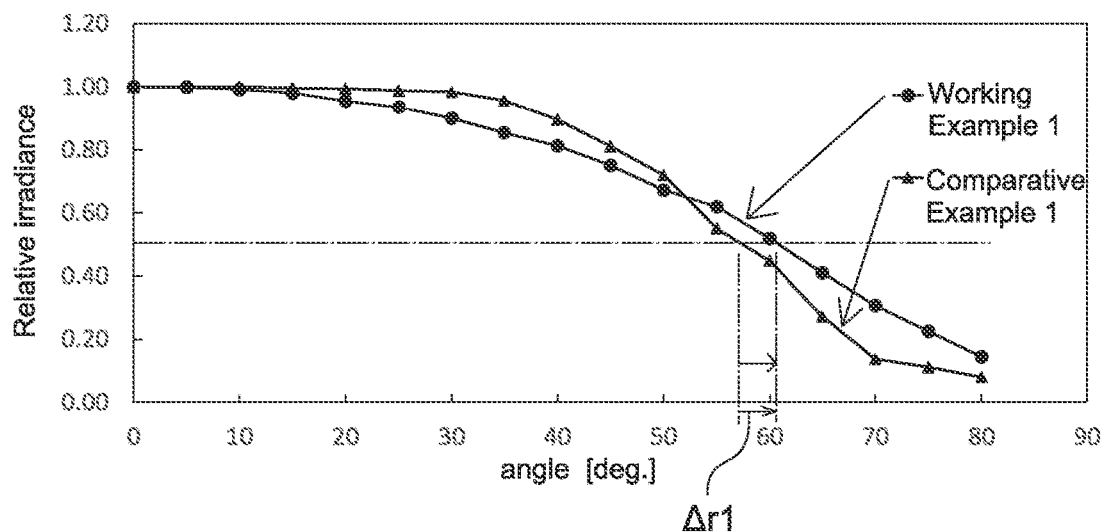
FIG. 17A Graph showing relative irradiance as a function of change in rotational angle at an ultraviolet light irradiation device that does not have an optical filter.
Figure 17B:
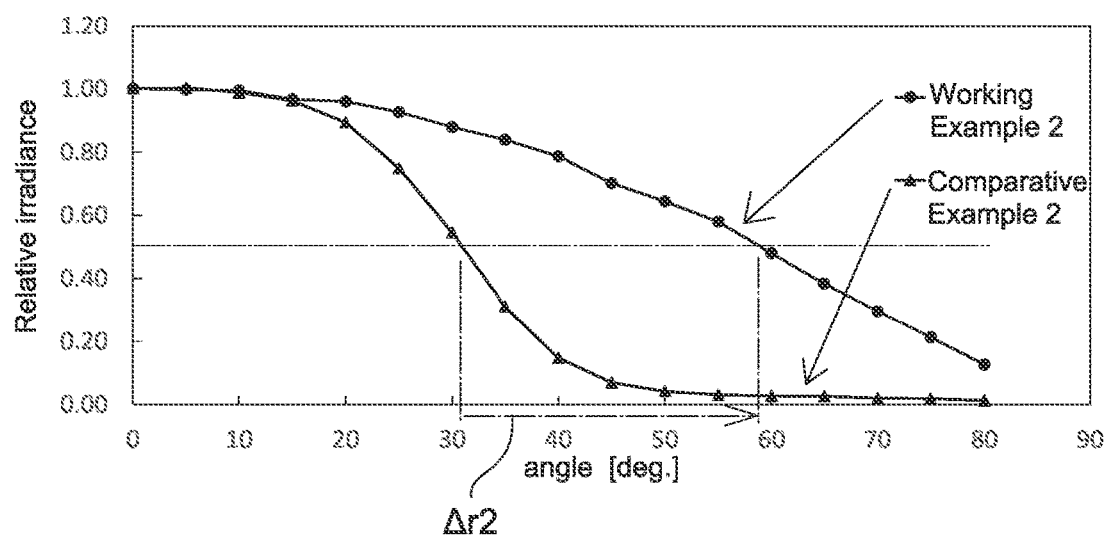
FIG. 17B Graph showing relative irradiance as a function of change in rotational angle at an ultraviolet light irradiation device that has an optical filter.
Figure 18:
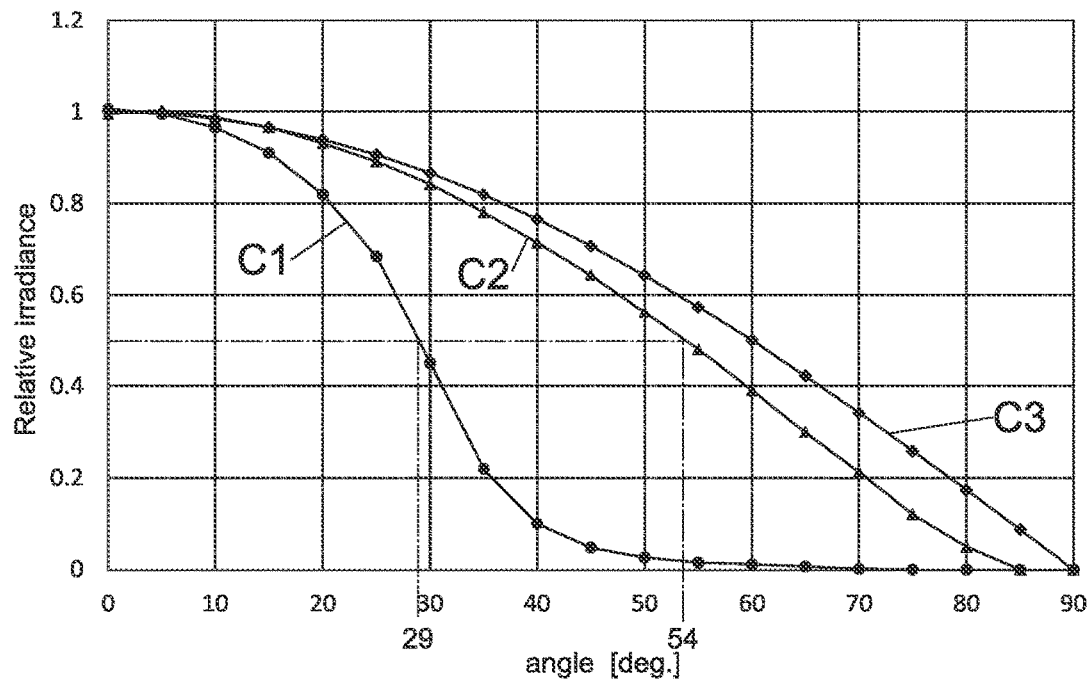
FIG. 18 Graph showing relative irradiance as a function of change in rotational angle.

Relative irradiance was calculated based on the results obtained from measurement of irradiance. Relative irradiance was calculated by dividing the value of irradiance measured at any given rotational angle by the value of irradiance measured when the rotational angle was 0° (deg). In other words, relative irradiance is the relative value of the irradiance of a ray proceeding at any given angle when the irradiance of a ray proceeding in the direction of the optical axis is taken to be 1. FIG. 17A, FIG. 17B, and FIG. 18 present graphs showing relative irradiance as a function of the change in rotational angle. Regarding the distance dl of the irradiance meter 31 from the ultraviolet light irradiation device 10, note that whereas FIG. 17A and FIG. 17B were based on conditions such that d1=300 (mm), FIG. 18 was based on conditions such that d1=1000 (mm).

With regard to the ultraviolet light irradiation devices that did not have an optical filter 6, referring to FIG. 17A, this indicates that Working Example 1 which had a diffusing member 5 exhibited relative irradiances that were higher over a wider range of angles than was the case for Comparative Example 1 which did not have a diffusing member 5. With regard to the rotational angle at which the relative irradiance was 0.50 (measured irradiance was half of the irradiance at a rotational angle of 0° (the optical axis)), that at Working Example 1 was larger than that at Comparative Example 1 by an amount corresponding to Δr1(=approximately) 4°. If angular divergence is assumed to be two times the rotational angle at which the relative irradiance was 0.50, it is fair to say that Working Example 1 had an angular divergence that was approximately 8° larger than that of Comparative Example 1. Based on this result, it is clear that provision of a diffusing member 5 caused the angular divergence to increase.

With regard to the ultraviolet light irradiation devices that did have an optical filter 6, referring to FIG. 17B, this indicates that Working Example 2 which had a diffusing member 5 exhibited relative irradiances that were higher over a wider range of angles than was the case for Comparative Example 2 which did not have a diffusing member 5. With regard to the rotational angle at which the relative irradiance was 0.50, that at Working Example 2 was larger than that at Comparative Example 2 by an amount corresponding to Δr2(=approximately) 28°. If angular divergence is assumed to be two times the rotational angle at which the relative irradiance was 0.50, it is fair to say that Working Example 2 had an angular divergence that was approximately 56° larger than that of Comparative Example 2. Based on this result, it is clear that provision of a diffusing member 5 caused the angular divergence to increase. Furthermore, upon comparison of Working Example 1 and Working Example 2, it is found that this increase in angular divergence was exhibited in especially remarkable fashion when an optical filter 6 was present.

FIG. 18 presents three curves. Curve C1 indicates the relative irradiance obtained based on the results of measurement using ultraviolet light irradiation device C1. Ultraviolet light irradiation device C1 was provided with an optical filter 6 but was not provided with a diffusing member 5.

Curve C2 indicates the relative irradiance obtained based on the results of measurement using ultraviolet light irradiation device C2. Ultraviolet light irradiation device C2 was provided with an optical filter 6 that transmitted ultraviolet light within a wavelength band of 190 nm to 235 nm but substantially did not transmit ultraviolet light within a wavelength band of 240 nm to 280 nm or less, and was provided with a diffusing member 5 including a PTFE sheet (of thickness 0.1 mm). Note that the PTFE sheet used here was a "Naflon PTFE Sheet" manufactured by Nichias Corporation (sheet thickness 0.1 mm).

Curve C3 is a luminous intensity distribution curve obtained by calculation for the ideal situation in which there is perfect diffusion. Such calculation was carried out based on the values of the cosines at the respective rotational angles.

From comparison of curve C1 and curve C3, it is clear that provision of an optical filter 6 caused the angular range of the relative irradiances to decrease relative to that of the luminous intensity distribution curve for the ideal situation in which there is perfect diffusion. However, upon further comparison with curve C2, it is clear that provision of a diffusing member 5 caused this to be a luminous intensity distribution curve for an ideal situation which was close to perfect diffusion.

Angular divergence was calculated as two times the rotational angle at which the relative irradiance was 0.50. From FIG. 18, the angular divergence of ultraviolet light irradiation device C1 was 58° (29×2), and the angular divergence of ultraviolet light irradiation device C2 was 108° (54×2). This confirms that provision of a diffusing member 5 caused a large increase in angular divergence.

Whereas the foregoing results were obtained with use of a PTFE sheet at the diffusing member 5, angular divergence also increased in similar fashion as was the case with PTFE sheet when a diffusing sheet other than PTFE sheet, or a diffusing film, was used at the diffusing member 5.

Figure 19:
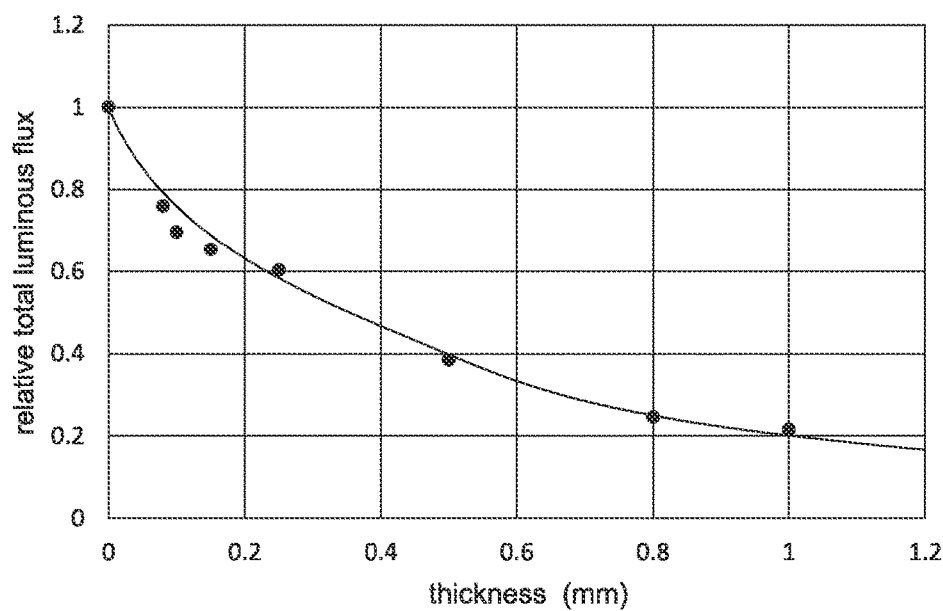
FIG. 19 Graph at which PTFE sheet thickness is plotted on the horizontal axis and relative total luminous flux is plotted on the vertical axis.

FIG. 19 shows the relative total luminous flux at an ultraviolet light irradiation devices in which PTFE sheets of varying thicknesses were used as diffusing members 5. FIG. 19 is a graph at which PTFE sheet thickness is plotted on the horizontal axis and relative total luminous flux is plotted on the vertical axis. Relative total luminous flux was calculated from the ratio of the total luminous flux that exited the ultraviolet light irradiation devices with the sheets of respective thicknesses to the total luminous flux exiting an ultraviolet light irradiation device in which no diffusing member was present. Total luminous flux indicates the sum of the luminous flux radiated in all directions from the light source, an approximation of which can be obtained as a result of calculation based on the irradiance values measured at the respective rotational angles using the measuring equipment 40 shown in FIG. 16.

Based on FIG. 19, relative total luminous flux decreases with increasing PTFE sheet thickness. This indicates that attenuation of ultraviolet light increases with increasing PTFE sheet thickness. When the PTFE sheet was less than 1 mm, relative total luminous flux was not less than 0.2, which is preferred. When the PTFE sheet was less than 0.5 mm, relative total luminous flux was not less than 0.4, which is more preferred. When the PTFE sheet was less than 0.2 mm, relative total luminous flux exceeded 0.6, which is still more preferred. Note that even where the PTFE sheet was made thin, there was almost no impairment of the near-perfect-diffusion luminous intensity distribution curve. Even where thickness of the PTFE sheet was made to be 0.05 mm, the luminous intensity distribution curve that was obtained was close to curve C2 at FIG. 17.

EXPLANATION OF REFERENCE NUMERALS

2 Housing
2a First frame

2b Second frame
3 Excimer lamp
4 Extracting portion
5 Diffusing member
5b Diffusing film
5s Diffusing sheet
6 Optical filter
10 Ultraviolet light irradiation device
11 Optical element
11a Optical lens
11b Reflector
13 Securing portion
15 Quartz glass
20 Ultraviolet light irradiation device
23 Securing portion
25 Protruding portion
30 Rotary stage
31 Irradiance meter
40 Measuring equipment
51 Attachment portion
52 Screw
60 Ultraviolet light irradiation device
70 Ultraviolet light irradiation device
80 Ultraviolet light irradiation device

The invention claimed is:
1. An ultraviolet light irradiation device, comprising:
a light source that radiates ultraviolet light with a wavelength in a range of 190 nm to 235 nm;
a housing that houses the light source;
an extracting portion that extracts the ultraviolet light that is radiated from the light source and causes it to be directed toward an exterior of the housing;
an optical filter that transmits ultraviolet light within a wavelength band of 190 nm to 235 nm but substantially does not transmit ultraviolet light within a wavelength band of 240 nm to 280 nm; and
a diffusing member that diffuses the ultraviolet light, wherein the diffusing member is arranged toward where the ultraviolet light exits the optical filter at the extracting portion, wherein the diffusing member is arranged so as to come in contact with the optical filter.
2. The ultraviolet light irradiation device according to claim 1, further comprising an optical filter that transmits ultraviolet light within a wavelength band of 190 nm to 235 nm but substantially does not transmit ultraviolet light within a wavelength band of 240 nm to 300 nm.
3. The ultraviolet light irradiation device according to claim 2, wherein
the optical filter and the diffusing member are arranged at the extracting portion; and
the optical filter is disposed between the light source and the diffusing member.
4. The ultraviolet light irradiation device according to claim 1, further comprising a reflecting member that is within the housing and that reflects light radiated by the light source.
5. The ultraviolet light irradiation device according to claim 1, wherein a primary material from which the diffusing member is constituted is quartz glass, fluororesin, polyethylene, or PET.
6. The ultraviolet light irradiation device according to claim 1, wherein the diffusing member is a diffusing sheet.
7. The ultraviolet light irradiation device according to claim 6, wherein a primary constituent of the diffusing sheet is PTFE.
8. The ultraviolet light irradiation device according to claim 6, further comprising: a securing portion that secures the diffusing sheet at a periphery of the extracting portion.
9. The ultraviolet light irradiation device according to claim 1, wherein the diffusing member is a diffusing film which is formed on the optical filter.
10. The ultraviolet light irradiation device according to claim 9, wherein a primary constituent of the diffusing film is silica or alumina.
11. The ultraviolet light irradiation device according to claim 1, wherein the diffusing member is arranged so as to be interposed between the optical filter and a transmissive plate that transmits the ultraviolet light.
12. The ultraviolet light irradiation device according to claim 1, wherein the diffusing member is less than 1 mm in thickness.
13. The ultraviolet light irradiation device according to claim 12, wherein the diffusing member is less than 0.5 mm in thickness.
14. The ultraviolet light irradiation device according to claim 1, wherein the light source is an excimer lamp.
15. A method of using an ultraviolet light irradiation device, comprising:
arranging the ultraviolet light irradiation device according to claim 1 such that irradiation by at least a portion of ultraviolet light that exits therefrom is directed toward a space used by humans,
causing the ultraviolet irradiation device to radiate the ultraviolet light.
16. An ultraviolet light irradiation device, comprising:
a light source that radiates ultraviolet light with a wavelength in a range of 190 nm to 235 nm;
a housing that houses the light source;
an extracting portion that extracts the ultraviolet light that is radiated from the light source and causes it to be directed toward an exterior of the housing;
an optical filter that transmits ultraviolet light within a wavelength band of 190 nm to 235 nm but substantially does not transmit ultraviolet light within a wavelength band of 240 nm to 280 nm; and
a diffusing member that diffuses the ultraviolet light, wherein the diffusing member is arranged toward where the ultraviolet light exits the optical filter at the extracting portion, wherein the diffusing member is arranged so as to come in contact with the optical filter,
wherein the housing has, at a location toward where the ultraviolet light exits the optical filter, an attachment portion for attachment of the diffusing member.
17. An ultraviolet light irradiation method, comprising:
causing ultraviolet light to be radiated from a light source housed in a housing that radiates ultraviolet light with a wavelength in a range of 190 nm to 235 nm;
extracting the ultraviolet light that is radiated from the light source and causing it to be directed toward an exterior of the housing;
causing the ultraviolet light radiated from the light source to be selectively transmitted by an optical filter that transmits ultraviolet light within a wavelength band of 190 nm to 235 nm but substantially does not transmit ultraviolet light within a wavelength band of 240 nm to 280 nm; and
causing light that exits the optical filter to be diffused by a diffusing member that is arranged toward an exit side of the optical filter, wherein the diffusing member diffuses the ultraviolet light, wherein the diffusing member is arranged so as to come in contact with the optical filter.

\* \* \* \* \*